(12) United States Patent
Chen et al.

(10) Patent No.: US 7,761,239 B2
(45) Date of Patent: Jul. 20, 2010

(54) METHOD OF DIAGNOSING BIOLOGICAL STATES THROUGH THE USE OF A CENTRALIZED, ADAPTIVE MODEL, AND REMOTE SAMPLE PROCESSING

(75) Inventors: Tzong-Hao Chen, North Potomac, MD (US); Ben A. Hitt, Wheeling, WV (US); Peter J. Levine, Potomac, MD (US)

(73) Assignee: Correlogic Systems, Inc., Germantown, MD (US)

( * ) Notice: Subject to any disclaimer, the term of this patent is extended or adjusted under 35 U.S.C. 154(b) by 1081 days.

(21) Appl. No.: 11/008,784

(22) Filed: Dec. 10, 2004

(65) Prior Publication Data
US 2005/0209786 A1   Sep. 22, 2005

Related U.S. Application Data

(60) Provisional application No. 60/528,478, filed on Dec. 11, 2003.

(51) Int. Cl.
*G06F 19/00* (2006.01)
*G06F 7/00* (2006.01)
*G01N 31/00* (2006.01)
*G01N 24/00* (2006.01)

(52) U.S. Cl. ............................ 702/19; 702/22; 702/27; 702/32; 436/173

(58) Field of Classification Search ................. None
See application file for complete search history.

(56) References Cited

U.S. PATENT DOCUMENTS

| | | | |
|---|---|---|---|
| 4,122,343 A | 10/1978 | Risby et al. | |
| 4,697,242 A | 9/1987 | Holland et al. | |
| 4,881,178 A | 11/1989 | Holland et al. | |
| 5,136,686 A | 8/1992 | Koza | |
| 5,352,613 A | 10/1994 | Tafas | |
| 5,649,030 A | 7/1997 | Normile | |
| 5,687,716 A | 11/1997 | Kaufmann et al. | |
| 5,697,369 A | 12/1997 | Long, Jr. et al. | |
| 5,716,825 A | 2/1998 | Hancock et al. | |
| 5,769,074 A | 6/1998 | Barnhill et al. | |
| 5,790,761 A | 8/1998 | Heseltine et al. | |
| 5,839,438 A | 11/1998 | Graettinger et al. | |
| 5,905,258 A | 5/1999 | Clemmer et al. | |
| 5,946,640 A | 8/1999 | Goodacre et al. | |
| 5,974,412 A | 10/1999 | Hazlehurst | |
| 6,025,128 A | 2/2000 | Veltri et al. | |
| 6,035,230 A | 3/2000 | Kang et al. | |
| 6,081,797 A | 6/2000 | Hitt | |
| 6,128,608 A | 10/2000 | Barnhill | |
| 6,157,921 A | 12/2000 | Barnhill | |
| 6,248,063 B1 | 6/2001 | Barnhill et al. | |
| 6,295,514 B1 | 9/2001 | Agrafiotis et al. | |
| 6,311,163 B1 | 10/2001 | Sheehan et al. | |
| 6,329,652 B1 | 12/2001 | Windig et al. | |
| 6,427,141 B1 | 7/2002 | Barnhill | |
| 6,558,902 B1 | 5/2003 | Hillenkamp | |
| 6,571,227 B1 | 5/2003 | Agrafiotis et al. | |
| 6,615,199 B1 | 9/2003 | Bowman-Amuah | |
| 6,675,104 B2 | 1/2004 | Paulse et al. | |
| 6,925,389 B2 * | 8/2005 | Hitt et al. ...................... | 702/19 |
| 7,333,896 B2 * | 2/2008 | Hitt et al. ...................... | 702/19 |
| 2002/0019023 A1 | 2/2002 | Dasseux et al. | |
| 2002/0046198 A1 | 4/2002 | Hitt | |
| 2002/0059030 A1 | 5/2002 | Otworth et al. | |
| 2002/0138208 A1 | 9/2002 | Paulse | |
| 2002/0193950 A1 | 12/2002 | Gavin et al. | |
| 2003/0004402 A1 | 1/2003 | Hitt et al. | |
| 2003/0054367 A1 | 3/2003 | Rich et al. | |

(Continued)

FOREIGN PATENT DOCUMENTS

WO   WO 93/05478 A1   3/1993

(Continued)

OTHER PUBLICATIONS

Loging, T.W. et al., "Identifying Potential Tumor Markers and Antigens by Database Mining and Rapid Expression Screening," *Genome Research*, 10(9):1393-402 (Sep. 2000).

(Continued)

*Primary Examiner*—Lori A Clow

(57) ABSTRACT

A model of a particular biological state can be developed. The model may be used to determine if an unknown biological sample exhibits a particular biological state. This can be done by receiving either a biological sample or data associated with the biological sample. After the data is received, the data may be input into the model. In one embodiment, the acquisition of the data associated with the biological sample is performed at a first location and the imputing of the data into the model is performed at a second location different than the first location. Unless the data maps identically to the model, the data would have an inherent effect on the position of the particular clusters within the discriminatory pattern, if it is allowed to affect the model. The modeling software can keep track of the net effect on the model that each sample received has on the position of the model. If the model has drifted outside of a predetermined tolerance, the model can be updated. Various business relationships may be developed to undertake various steps of the overall method for providing a diagnosis to a patient.

7 Claims, 10 Drawing Sheets

U.S. PATENT DOCUMENTS

| | | |
|---|---|---|
| 2003/0077616 A1 | 4/2003 | Lomas |
| 2003/0129589 A1 | 7/2003 | Koster et al. |
| 2003/0134304 A1 | 7/2003 | van der Greef |
| 2004/0116797 A1 | 6/2004 | Takahashi et al. |
| 2004/0260478 A1 | 12/2004 | Schwamm |

FOREIGN PATENT DOCUMENTS

| | | |
|---|---|---|
| WO | WO 99/41612 | 8/1999 |
| WO | WO 99/47925 A2 | 9/1999 |
| WO | WO 99/58972 A1 | 11/1999 |
| WO | WO 00/49410 A3 | 8/2000 |
| WO | WO 00/55628 A1 | 9/2000 |
| WO | WO 01/20043 A1 | 3/2001 |
| WO | WO 01/31579 A2 | 5/2001 |
| WO | WO 01/31580 A2 | 5/2001 |
| WO | WO 01/84140 A2 | 11/2001 |
| WO | WO 02/06829 A2 | 1/2002 |
| WO | WO 02/059822 A2 | 8/2002 |
| WO | WO 02/088744 A2 | 11/2002 |
| WO | WO 03/031031 A1 | 4/2003 |
| WO | WO 2004/103163 A2 | 12/2004 |
| WO | WO 2006/006176 A2 | 1/2006 |

OTHER PUBLICATIONS

Krishnamurthy, T. et al., "Detection of Pathogenic and Non-Pathogenic Bacteria by Matrix-assisted Laser Desorption.Ionization Time-of-flight Mass Spectrometry," *Rapid Comms. in Mass Spectrometry*, 10:883-888 (1996).

Adam, B-L et al., "Serum Protien Fingerprinting Coupled with a Pattern-matching Algorithm Distinguishes Prostate Cancer from Benign Prostate Hyperplasia and Healthy Men," *Cancer Research*, 62:3609-3614 (Jul. 1, 2002).

Li, J. et al., "Proteomics and Bioinformatics Approaches for Identification of Serum Biomarkers to Detect Breast Cancer," *Clinical Chemistry*, 48(8):1296-1304 (2002).

Petricion III, E.F. et al., "Use of proteomic patterns in serum to identify ovarian cancer," *The Lancet*, 359:572-577 (Feb. 16, 2002).

Brown, M.P.S. et al. "Knowledge-based analysis of microarray gene expression data by using support vector machines," *PNAS*, 97(1):262-267 (Jan. 4, 2000).

Kiem, H. & Phuc, D, "Using Rough Genetic and Kohonen's Neural Network for Conceptual Cluster Discovery in Data Mining," New Directions in Rough Sets, Data Mining and Granular-Soft Computing. International Workshop, RSFDGRC Proceedings, pp. 448-452 (Nov. 9, 1999).

Chang, E.I et al., "Using Genetic Algorithms to Select and Create Features for Pattern Classification," *IJCNN International Joint Conf. On Neural Networks*, pp. III-747 to III-752 (Jun. 17-21, 1990).

Rosty C. et al., "Identification of Hepatocarcinoma-Intestine-Pancreas/Pancreatitis-associated Protein I as a Biomarker for Pancreatic Ductal Adenocarcinoma by Protein Biochip Technology," *Cancer Research*, 62:1868-75 (Mar. 15, 2002).

Claydon, M.A., "The rapid identification of intact microorganisms using mass spectrometry," *Nature Biotech*, 14:1584-1586 (Nov. 1996).

Bittl, J.A., "From Confusion to Clarity: Direct Thrombin Inhibitors for Patients with Heparin-Induced Thrombocytopenia," *Cath. and Cardio. Interventions*, 52:473-475 (2001).

Paweletz, C.P., Rapid Protein Display Profiling of Cancer Progression Directly from Human Tissue Using a Protein Biochip, *Drug Development Research*, 49:34-42 (2000).

Ciphergen European Update, 1:1-4 (2001).

Kohonen, T. Self Organizing Maps (Springer 2001), pp. 1-70.

Zhang, *Dynamics and Formation of Self-Organizing Maps*, in "Self-Organizing Map Formation: Foundations of Neural Computation," pp. 55-67 (Klaus Obermayer & Terrence J. Sejnowski eds.), 2001 annotated by LAC.

Kohonen, T. "Self-Organization and Associative Memory" (Springer 1988), pp. 30-67.

Holland, J.H., "Adaption in Natural and Artificial Systems: An Introductory Analysis with Applications to Biology, Control, and Artificial Intelligence" (MIT Press 2001), pp. 1-31; 89-119.

Claydon et al. "The Rapid Identification of Intact Microorganisims Using Mass Spectrometry," Nat. Biotechnol. Nov. 1996, Abstratct (1 page).

Yao et al. "Evolving Artificial Neural Networks for Medicla Applications." Proc. of the First Korea-Australia Joint Workshop on Evolutionary Computation, Sep. 1995, pp. 1-16.

Goodacre et al. "Rapid Identification of Urinary Tract Infection Bacteria using Hyperspectral Whole-Organism Fingerprinting and Artificial Neural Networks," *Microbiology*, 144:1157-70 (1998).

Pei et al. "Feature Extraction Using Genetic Algorithms," Proceedings of the First International Symposium on Intelligent Data Engineering and Learning, IDEAL '98, Springer, Hong Kong, Oct. 1998, pp. 371-384.

Jain et al. "Statistical Pattern Recognition: A Review," *IEEE Trans. on Pattern Analysis and Machine Intelligence*, 22(1):4-37 (Jan. 2000).

Hackett et al. "Rapid SELDI Biomarker Protien Profiling of Serum from Normal and Prostate Cancer Patients," *American Ass 'n for Cancer Research*, 41:563-564 (Mar. 2000) (Abstract only).

Microsoft Press, Computer Dictionary, Microsoft Press (1994), pp. 87 & 408.

Gaskell, "Electrospray: Principles and Practice," *Journal of Mass Spectrometry*, 32:677-688 (1997), John Wiley & Sons, Ltd.

Lewis, "An Introduction to Classification and Regression Tree (CART) Analysis," presented at 2000 Annual Meeting of the Society for Academic Emergency Medicine in San Francisco, California, pp. 1-14, 2000.

Hess et al., "Classification and Regression Tree Analysis of 1000 Consecutive Patients with Unknown Primary Carcinoma," *Clinical Cancer Research*, 5:3403-3410 (Nov. 1999).

Schroll et al., "Applications of Artificial Intelligence for Chemical Inference, III. Aliphatic Ethers Diagnosed by Their Low-Resolution Mass Spectra and Nuclear Magnetic Resonance Data," *Journal of the American Chemical Society*, (Dec. 17, 1969), pp. 7440-7445.

Crawford et al., "Computer Methods in Analytical Mass Spectrometry; Empirical Identification of Molecular Class," 6 pages (1968).

Jurs et al., "Computerized Learning Machines Applied to Chemical Problems; Molecular Formula Determination from Low Resolution Mass Spectrometry," *Analytical Chemistry*, 41( I ):21-27 (Jan. 1969).

Meuzelaar et al., "A Technique for Fast and Reproducible Fingerprinting of Bacteria by Pyrolysis Mass Spectrometry," *Analytical Chemistry*, 45(3):587-590 (Mar. 1973).

Gray, N.A.B. "Constraints on 'Learning Machine' Classification Methods," *Analytical Chemistry*, 48(14):2265-2268 (Dec. 1976).

Lowry et al., "Comparison of Various K-Nearest Neighbor Voting Schemes with the Self-Training Interpretive and Retrieval System for Identifying Molecular Substructures from Mass Spectral Data," *Analytical Chemistry*, 49(12):1720-1722 (1977).

MacFie et al., "Use of Canonical Variates Analysis in Differentiation of Bacteria by Pyrolysis Gas-Liquid Chromatography," *Journal of General Microbiology*, 104: 67-74, Great Britain (1978).

Atkinson et al., "Statistical Techniques for Diagnosing CIN Using Fluorescence Spectroscopy: SVD and CART," *Journal of Cellular Biochemistry*, Supplement 23, pp. 125-130 (1995).

Dzeroski et al., "Diterpene Structure Elucidation from $^{13}$C NMR-Spectra with Machine Learning," *Intelligent Data Analysis in Medicine and Pharmacology*, pp. 207-225, Kluwer Academic Publishers (1997).

Voorhees et al., "Approaches to Pyrolysis/Mass Spectrometry Data Analysis of Biological Materials," *Computer-Enhanced Analytical Spectroscopy*,2: 259-275, Plenum Press, New York (1990).

Reibnegger et al., "Neural networks as a tool for utilizing laboratory information: Comparison with linear discrminant analysis and with classification and regression trees," *Proc. Natl. Acad. Sci. USA*, 88:11426-11430 (Dec. 1991).

Jellum et al., "Mass Spectrometry in Diagnosis of Metabolic Disorders," *Biomedical and Environmental Mass Spectrometry*, 16: 57-62 (1988).

Wythoff et al., "Spectral Peak Verification and Recognition Using a Multilayered Neural Network," *Analytic Chemistry*, 62(24:2702-2709 (Dec. 15, 1990).

Meyer et al., "Identification of the ¹H-NMR Spectra of Complex Oligosaccharides with Artificial Neural Networks," *Science*, 251:542-544 (Feb. 1991).

Furlong et al., "Neural Network Analysis of Serial Cardiac Enzyme Data; A Clinical Application of Artificial Machine Intelligence," A.J.C.P., 96(1):134-141 (Jul. 1991).

Cicchetti, "Neural Networks and Diagnosis in the Clinical Laboratory: State of the Art," *Clinical Chemistry*, 38(1): 9-10 (1992).

Ashfaq et al., "Evaluation of PAPNET™ System for Rescreening of Negative Cervical Smears," *Diagnostic Cytopathology*, 13(1): 31-36 (1995).

Malins et al., "Models of DNA structure achieve almost perfect discrimination between normal prostrate, benign prostatic hyperplasia (BPH), and adenocarcinoma and have a high potential for predicting BPH and prostrate cancer," *Proc. Nat. Acad. Sci. USA*, 94:259-264 (Jan. 1997).

Ricketts et al., "Towards the Automated Prescreening of Cervical Smears," 4 pages, Mar. 11, 1992.

Kohno et al., "Quantitative Analysis of Scintiscan Matrices by Computer," *Japanese Journal of Medical Electronics and Biological Engineering*, pp. 22-29 (Aug. 1974).

Salford Systems, "Salford Systems White Paper Series," 17 pages (2000).

Berikov et al., "Regression trees for analysis of mutational spectra in nucleotide sequences," *Bioinformatics*, 15(7/8):553-562 (1999).

Breiman et al., *Classification and Regression Trees*, pp. 174-265, Chapman & Hall/CRC (1998).

Halket et al., "Deconvolution Gas Chromatography/Mass Spectrometry of Urinary Organic Acids—Potential for Pattern Recognition and Automated Identification of Metabolic Disorders," *Rapid Communications in Mass Spectrometry*, vol. 13, pp. 279-284 (1999).

Eghbaldar et al., "Identification of Structural Features from Mass Spectrometry Using a Neural Network Approach: Application to Trimethylsilyl Derivatives Used for Medical Diagnosis," *J. Chem. Inf. Comput. Sci.*, 36(4):637-643 (1996).

Babaian, et al., "Performance of a Neural Network in Detecting Prostate Cancer in the Prostate-Specific Antigen Reflex Range of 2.5 to 4.0 ng/ml," *Urology*, 56(6):1000-1006 (2000).

Tong et al., "Mass Spectral Search method using the Neural Network approach," *International Joint Conference on Neural Networks*, Washington, DC Jul. 10-16, 1999, Proceedings, vol. 6 of 6, pp. 3962-3967.

Tong et al., "Mass spectral search method using the neural network approach," *Chemometrics and Intelligent Laboratory Systems*, 49:135-150 (1999).

Hashemi et al., "Identifying and Testing of Signatures for Non-Volatile Biomolecules Using Tandem Mass Spectra," *SIGBIO Newsletter*, 15(3):11-19 (1995).

Belic et al., "Neural network methodologies for mass spectra recognition," *Vacuum*, 48(7-9):633-637 (1997).

Werther et al., "Classification of mass spectra; a comparison of yes/no classification methods for the recognition of simple structural properties," *Chemometrics and Intelligent Laboratory Systems*, 22:63-76 (1994).

Cairns et al., "Towards the Automated Prescreening of Breast X-Rays," 5 pages (Mar. 11, 1992).

Astion et al., "The Application of Backpropagation Neural Networks to Problems in Pathology and Laboratory Medicine," *Arch Pathol Lab Med*, 116:995-1001 (Oct. 1992).

Taylor et. al., "The Deconvolution of Pyrolysis Mass Spectra Using Genetic Programming: Application to the Identification of Some *Eubacterium* Species," *FEMS Microbiology Letters*, 160:237-246 (1998).

Goodacre et al., "Discrimination between methicillin-resistant and methicillin-susceptible *Staphylococcus aureus* using pyrolysis mass spectrometry and artificial neural networks," *Journal of Antimicrobial Chemotherapy*, 41:27-34 (1998).

Chun et al., "Long-term Identification of Streptomycetes Using Pyrolysis Mass Spectrometry and Artificial Neural Networks," Zbl. Bakt. 285, pp. 258-266 (1997).

Kenyon et al., "Application of Neural Networks to the Analysis of Pyrolysis Mass Spectra," Zbl. Bakt. 285, pp. 267-277 (1997).

Nilsson et al., "Classification of Species in the Genus Penicillium by Curie Point Pyrolysis/Mass Spectrometry Followed by Multivariate Analysis and Artificial Neural Networks," *Journal of Mass Spectrometry*, 31:1422-1428 (1996).

Goodacre et al., "Sub-species Discrimination, Using Pyrolysis Mass Spectrometry and Self-organising Neural Networks, of *Propionibacterium acnes* Isolated from Normal Human Skin," Zbl. Bakt. 284, pp. 501-515 (1996).

Goodacre et al., "Quantitative Analysis of Multivariate Data Using Artificial Neural Networks: A Tutorial Review and Applications to the Deconvolution of Pyrolysis Mass Spectra," Zbl. Bakt. 284 pp. 516-539 (1996).

Goodacre et al., "Identification and Discrimination of Oral Asaccharolytic *Eubacterium* spp. by Pyrolysis Mass Spectrometry and Artificial Neural Networks," *Current Microbiology*, 32:77-84 (1996).

Goodacre et al., "Correction of Mass Spectral Drift Using Artificial Neural Networks," *Anal. Chem.*, 68:271-280 (1996).

Freeman et al., "Resolution of batch variations in pyrolysis mass spectrometry of bacteria by the use of artificial neural network analysis," *Antonie van Leeuwenhoek*, 68:253-260 (1995), Kluwer Academic Publishers, The Netherlands.

Chace et al., "Laboratory integration and utilization of tandem mass spectrometry in neonatal screening: a model for clinical mass spectrometry in the next millennium," *Acta Paediatr. Suppl.* 432, pp. 45-47 (1999).

Curry et al., "MSnet: A Neural Network That Classifies Mass Spectra," 32 pages (1990).

Shaw et al., "Infrared Spectroscopy of Exfoliated Cervical Cell Specimens," *Analytical and Quantitative Cytology and Histology*, 21(4):292-302 (1999).

Belic, "Neural Networks Methodologies for Mass Spectra Recognition," pp. 375-380, 1997 annotated LAC.

Prior et al., "Potential of Urinary Neopterin Excretion in Differentiating Chronic Non-A, Non-B Hepatitis from Fatty Liver," *The Lancet*, Nov. 28, 1987, pp. 1235-1237.

Yates, III, "Mass Spectrometry and the Age of the Proteome," *Journal of Mass Spectrometry*, 33:1-19 (1998).

Hausen et al., "Determination of Neopterine in Human Urine by Reversed-Phase High-Performance Liquid Chromatography," *Journal of Chromatography*, 227:61-70 (1982).

Shevchenko et al., "MALDI Quadupole Time-of-Flight Mass Spectrometry: A Powerful Tool for Proteomic Research," *Anaytical Chemistry*, 72(9): 2132-2141 (May 1, 2000).

Dudoit et al., "Comparison of Discrimination Methods for the Classification of Tumors Using Gene Expression Data," 43 pages, Jun. 2000.

Dudoit at al., "Comparison of discrimination methods for the classification of tumors using gene expression data," UC Berkeley, Mar. 7, 2000, pp. 1-51.

Nikulin et al., "Near-optimal region selection for feature space reduction: novel preprocessing methods for classifying MR spectra," *NMR Biomedicine*, 11:209-216 (1998).

Alaiya et al., "Classification of Human Ovarian Tumors Using Multivariate Data Analysis of Polypeptide Expression Patterns," *Int. J. Cancer*, 86:731-736 (2000).

Bailey-Kellogg et al., "Reducing Mass Degeneracy in SAR by MS by Stable Isotopic Labeling," *Journal of Computational Biology*, 8(1):19-36 (2001).

Caprioli et al., "Molecular Imaging of Biological Samples: Localization of Peptides and Proteins Using MALDI-TOF MS," *Analytical Chemistry*, 69(23):4751-4760 (Dec. 1, 1997).

George, "A Visualization and Design Tool (AVID) for Data Mining with the Self-Organizing Feature Map," *International Journal on Artificial Intelligence Tools*, 9(3): 369-375 (2000).

Kohavi, et al., "Wrappers for feature subset selection," *Artificial Intelligence*, 97:273-324 (1997).

Marvin et al., "Characterization of a novel *Sepia officinalis* neuropeptide using MALDI-TOL MS and post-source decay analysis," *Peptides*, 22:1391-1396 (2001).

Oh et al., "A database of protein expression in lung cancer," *Proteomics*, 1:1303-1319 (2001).

Strouthopoulos et al., "PLA using RLSA and a neural network," *Engineering Applications of Artificial Intelligence*, 12:119-138 (1999).

Zhang, "Combining Multiple Biomarkers in Clinical Diagnostics—A Review of Methods and Issues," 14 pages (2002).

vonEggeling et al., "Mass Spectrometry Meets Chip Technology: A New Proteomic Tool in Cancer Research?" *Electrophoresis*, 22:2898-2902 (2001).

Petricoin III, E.F. et al., "Serum Proteomic Patterns for Detection of Prostate Cancer," *Journal of the National Center Institute*, 94(20) (2002).

Zhang et al., "Proteomics and Bioinformatics Approaches for Identification of Serum Biomarkers to Detect Breast Cancer," *Clinical Chemistry*, 48(8):1296-1304 (2002).

Dhar et al., Seven Methods for Transforming Corporate Data Into Business Intelligence, Prentice Hall, pp. 52-76, (1997).

Reed, "Trends in Commercial Bioinformatics," *Oscar Gruss Biotechnology Review*, Mar. 2000, 20 pages.

Lockhart, D.J. et al., "Genomics, Gene Expression and DNA Arrays," *Nature*, 405:827-836 (2000).

Roses, A.D., "Pharmacogenetics and the Practice of Medice," *Nature*, 405:857-865 (2000)/.

Moler E.J. et al., "Analysis of Molecular Profile Data Using Generative and Discriminative Methods," *Physiol Genomics*, 4:109-126 (2000)/.

Liotta et al., "Molecular Profiling of Human Cancer," *Nature Genetics*, 1:48-56 (2000).

Balteskard, L. et al., "Medical Diagnosis in the Internet Age," The Lancet, Dec. 1999, p. SIV14, vol. 354.

International Search Report dated Jun. 26, 2006, for International Application No. PCT/US04/41135, 2 pages.

Petricoin, E. F. et al., "Clinical Applications of Proteomics," Supplement: Nutritional Genomics and Proteomics in Cancer Prevention, Journal of Nutrition [online], Jul. 2003 [retrieved on Jan. 18, 2008], pp. 1-16, vol. 133, No. 7. Retrieved from the Internet: <URL: http://www.nutrition.org/cgi/content/full/133/7/2476S.

* cited by examiner

METHOD OF DIAGNOSING BIOLOGICAL STATES THROUGH THE USE OF A CENTRALIZED, ADAPTIVE MODEL, AND REMOTE SAMPLE PROCESSING

CROSS-REFERENCE TO RELATED APPLICATIONS

This application is based on and claims priority to U.S. Provisional Patent Application No. 60/528,478, entitled "Method Of Diagnosing Biological States Through The Use Of A Centralized, Adaptive Model, And Remote Sample Processing," filed on Dec. 11, 2003.

FIELD OF THE INVENTION

This invention relates generally to a system for the remote collection, selection, transmittal, and analysis of biological data through use of a centralized bioinformatics modeling system. More specifically, the invention relates to a method of refining a bioinformatic modeling system. The invention also relates to organizational mechanisms for carrying out portions of the diagnosis and modeling. Finally, the invention relates to a system or method of collecting data at a first location and transmitting the data to a second location for analysis in a modeling system.

BACKGROUND OF THE INVENTION

Methods of analyzing biological samples are generally known. In a typical analysis, a high-throughput bioassay, such as mass spectroscopy, may be performed on the biological sample to separate and quantify at least some of its constituent biochemical components (e.g. proteins, protein fragments, DNA, RNA, etc.). Based on the output of the bioassay, such as a mass spectrum, various diagnostics may be run. For example, a diagnostic model of a particular disease state may be applied to the mass spectrum to identify the sample from which the spectrum was derived as being taken from a subject that has, or does not have, the disease state. In some of the known methods of analyzing biological samples, the acquisition of the data (i.e., the performance of a high-throughput bioassay) and the analysis of the data (i.e., the application of the diagnostic model) are accomplished at the same location.

Such diagnostic models have been static, in that each such model is based on analysis of a finite set of biological samples with known attributes relevant to the disease state modeled (i.e. known to have or not to have the disease state) and is then used to assess biological samples for which the disease state is not known. Such an approach assumes that the sample set used to develop the diagnostic model is representative of the population from which unknown samples will be drawn for analysis by the model. If this assumption proves not to be valid, the model's validity and utility is questionable.

There is a need for a method of monitoring or evaluating the applicability of a diagnostic model to new, unknown biological samples and for determining whether/when a diagnostic model should be updated to reflect the differences between the original sample set and the population from which new, unknown samples have been drawn. There is further a need for generating a new model that reflects biological samples in addition to those from which the original model was created. Finally, there is a need for a method of analyzing biological samples that includes acquiring the data at a first location, transmitting a subset of the data to a second location different than the first location, and analyzing the data at the second location.

SUMMARY OF THE INVENTION

A diagnostic model can be built to determine if a biological sample exhibits a particular biological state. To build the model, a number of samples having a known biological state can be analyzed and input into a modeling program to find discriminatory patterns that are specific to a particular biological state.

An example of diagnostic modeling and pattern recognition technology that may be used to determine whether a sample has a particular biological state is the Knowledge Discovery Engine ("KDE"), which is disclosed in U.S. patent application Ser. No. 09/883,196, now U.S. Pat. No. 7,096,206, entitled "Heuristic Methods of Classification," filed Jun. 19, 2001 ("Heuristic Methods"), and U.S. patent application Ser. No. 09/906,661, now U.S. Pat. No. 6,925,389, entitled "A Process for Discriminating Between Biological States Based on Hidden Patterns from Biological Data," filed Jul. 18, 2001 ("Hidden Patterns"), the contents of both of which are hereby incorporated by reference in their entirety. Software implementing the KDE is available from Correlogic Systems, Inc, under the name PROTEOME QUEST™ algorithm.

After being developed, the model may be used to determine if a new biological sample whose state is unknown exhibits a particular biological state. Data characterizing the biological sample (e.g. from a bioassay such as a mass spectrum) can be compared to the model, and an assessment made of whether the sample falls within one of the diagnostic clusters that make up the model. Further, an assessment of the continuing viability of the model can be made by recalculating the location of the model's constituent diagnostic clusters by recalculating each cluster's position if it incorporates the unknown sample's data. This recalculation can be repeated for each unknown sample. If the location of any cluster's centroid as recalculated using the additional, unknown samples moves away from the original centroid by more than a predetermined tolerance, a determination can be made that the model does not accurately reflect the population from which the unknown samples have been taken, and that the model should be updated. An updated, or new, model can then be created based on the original sample set and some or all of the additional samples that have been analyzed by the original model.

The various portions of the acquiring, diagnostic, monitoring, and updating methods can be performed by one or more than one entity, and, various relationships can be defined between and among entities that specialize in providing models, collecting samples, performing high-throughput bioassay processes, diagnosing subjects using the models, monitoring drift or changes in the model, and updating the model. For example, in one embodiment, a first entity acquires data that characterizes a biological data. A subset of the acquired data is then sent (i.e., via an internet or an intranet) to a second entity. The second entity applies the transmitted data to a model and makes a diagnosis. The diagnosis is then transmitted from the second entity to the first entity. In one embodiment, the first entity is located remotely from the second entity.

DETAILED DESCRIPTION

Figure 1:
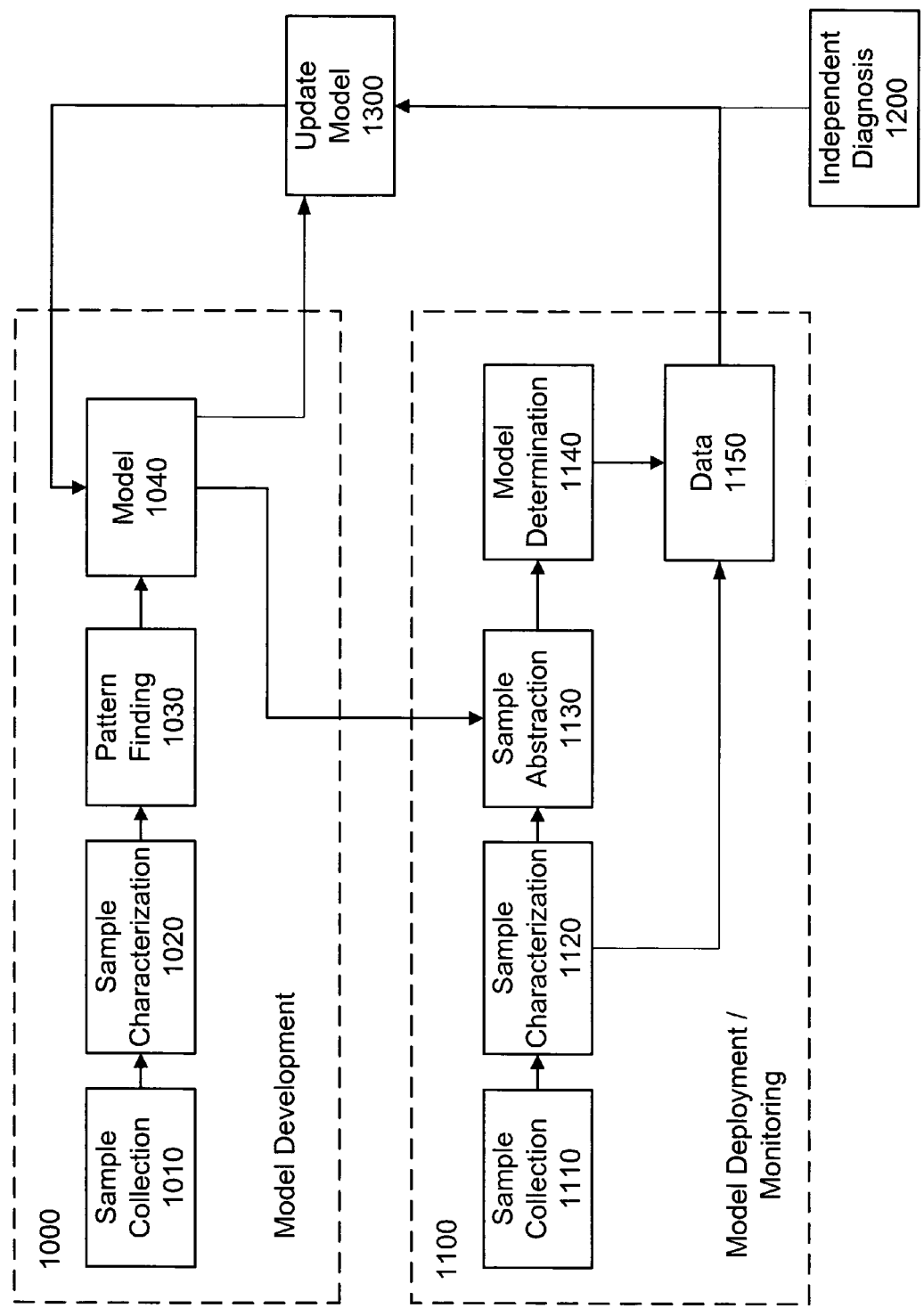
FIG. 1 is a process diagram of the process of developing a model, deploying the model, and updating the model according to an embodiment of the invention.

Generally, the invention includes a method of determining the biological state of an unknown sample using a diagnostic model based on an initial set of biological samples taken from subjects having known biological states, using unknown samples to assess the continuing validity of the assumption that the initial sample set accurately reflects the population from which the unknown samples are taken and to determine whether the model should be updated, and updating the model using at least some of the new biological samples.

Various terms are used herein to describe diagnostic models and their development, monitoring, and updating.

As used herein, the term "feature" refers to a value from among a range of values produced by a bioassay of a sample. For example, in the case of a mass spectrum derived from a sample by a protein separation technique, the mass spectrum is defined by a range of mass-to-charge (m/z) values, and a feature is a particular m/z value.

As used herein the term "vector" refers to a feature and an associated magnitude. Thus, for a mass spectrum, a vector is a two-dimensional value having both a mass-to-charge value and a magnitude or amplitude associated with it.

As used herein the term "pattern" refers to a collection of one or more vectors characterizing one or more biological samples.

As used herein the term "cluster" refers to a sphere (in three dimensional space) or a hypersphere (in n-dimensional space) centered on a centroid. A centroid is thus a point in n-dimensional space. Each dimension in the n-dimensional space may correspond to a feature, and thus any point in the n-dimensional space may be defined by a set of vectors. Thus, a biological sample characterized by, for example, a mass spectrum may be defined by a point in n-dimensional space, which point is the location defined by the vectors for the sample determined from the features to which the dimensions of the space correspond. A centroid, and thus an associated cluster, may be defined by the weighted average of vectors from characterizing spectra from multiple samples. Thus, a diagnostic model based on a set of known biologic samples may include a cluster that is defined by the weighted average of vectors for a subset of the samples. The subset of samples may be those for which each sample's characterizing vectors lie within a hypersphere of predetermined radius about the centroid defined by the samples' vectors.

As used herein, the term "model" refers to a collection of one or more clusters in an n-dimensional space, where the dimensions of the space, and the centroids of the clusters, are determined from data derived from a bioassay from a set of biologic samples taken from subjects having known values for the disease of or other biological state of which the model is to be diagnostic. The, or each, cluster of the model is associated with a value for the biological state, e.g. as having or not having a particular disease. The term "model" may also refer to a plurality of the above cluster models combined into a super-model.

FIG. 1 is a process diagram illustrating the process of developing a model, deploying the model, monitoring the model, and, as needed, refining or updating the model according to one embodiment of the invention. The first step is to develop the model, as shown in the steps grouped at 1000, as illustrated in FIG. 1. To do this, multiple samples are received at step 1010. Each sample is then characterized at step 1020 by a bioassay, such as a mass spectrum based on protein separation. The protein separation may be performed by a chip-based technique such as SELDI or MALDI, or by an electrospray ionization (ESI) process. The resultant mass spectrum is a multitude of mass-to-charge values and associated amplitudes or magnitudes that collectively characterize the biological sample. These mass-to-charge values and associated amplitudes can be input into a pattern recognition or finding program at step 1030. One suitable technology that may be used to identify patterns in the spectral data is the KDE identified above.

In general the KDE will search for patterns of molecular expression that are "diagnostic," i.e. that accurately differentiate the samples into desired diagnostic categories, such as "having ovarian cancer" or "not having ovarian cancer." Operation of the KDE is described in the Heuristic Methods and Hidden Patterns applications, and is not repeated in detail here.

The KDE will accept bioassay data (such as the mass-to-charge values and associated amplitudes) and seek to identify clusters of data (i.e., hidden patterns) in n-dimensional space, where n is the number of mass-to-charge values selected from the spectra, and each spectrum can be mapped into the n-dimensional space using the magnitude of each of the selected mass-to-charge values. Each cluster is preferably homogeneous with respect to the biological states that the model is intended to differentiate. For example, in one embodiment, a model will have at least one cluster into which are mapped only the samples corresponding to subjects having a disease of interest and at least one cluster into which are mapped only the samples corresponding to subjects not having the disease of interest. In another embodiment, the model is intended to differentiate between biological samples that includes a pathogen, such as anthrax, and samples that do not include the pathogen.

The KDE thus may be used to discover hidden patterns located within the data obtained from the biological samples. Based on these hidden patterns, the KDE determines a model for a particular biological state, step 1040.

The steps of acquiring samples at step 1010, characterizing the samples using a bioassay technique such as protein separation and mass spectrum analysis at step 1020, and finding patterns within the data 1030 are performed for any number of samples. In general, the more samples used to develop the model, the more robust the model can be, thereby increasing its sensitivity and specificity in accurately identifying the state of an biologic sample for which the state is unknown.

After the model has been developed for a particular biological state, the model may then be deployed as shown in the steps grouped as 1100 to diagnose a biological state associated with unknown samples. In the model deployment stage 1100, a sample of unknown state is received at step 1110. In the same manner as described above the sample is characterized at step 1120. Once these characterization data are obtained, the sample is abstracted at step 1130 by obtaining from the characterization data the vectors relevant to the model. Thus, for each dimension (i.e. feature) of the model, the amplitude for the corresponding mass-to-charge value is determined. The vectors for the sample are then mapped into the n-dimensional space of the model and a determination is made at step 1130 whether the sample vectors map into one of the clusters of the model. Based on this comparison of the point in space defined by the abstracted sample vectors to the cluster(s) of the model, a determination is made at step 1140 of the biological state of the subject from which the sample was taken. In each model, there is preferably at least one cluster that, if mapped to, will indicate that the biological sample is associated with a particular tested for disease state (e.g. a sample is identified as being taken from a subject having ovarian cancer). Each model preferably also has at least one control cluster, that if mapped to, indicates that the biological sample does not exhibit the tested for disease state. Alternatively, if the abstracted vectors map outside of any of the clusters of the model, a result of "indeterminate" may be returned, meaning that the vectors from the data associated with the biological sample did not map to any clusters within the model.

In addition to performing a diagnostic function, the diagnostic tool or software can be self monitoring. For example, data received from the sample abstraction step 1130, may be compared to the model data. Based on this comparison, the software can make an assessment of whether the new, unknown sample indicates that the known sample set used to develop the model is not sufficiently representative of the population from which unknown samples are drawn. One suitable technique for making this assessment is to recalculate the centroid of the model's cluster into which the unknown sample maps by combining the unknown sample's vectors with those of the sample set used to build the model. Then, the difference (if any) between the position of the recalculated centroid and the position of the original centroid can be calculated, and this difference compared to a predetermined tolerance or threshold. If the difference in the centroid positions exceeds the predetermined tolerance, then the model may need to be updated, as will be described in additional detail below. For example, in one embodiment, when the difference between the position of the recalculated centroid and the position of the original centroid exceeds the predetermined tolerance an output, such as a visual output on a display of a computer (for example as described in more detail in connection with FIG. 10), is produced. Additionally, when the difference between the position of the recalculated centroid and the position of the original centroid does not exceed the predetermined tolerance an output, such as a visual output, is produced.

The samples to which the diagnostic model are applied may be used to update the model if and when determined to be appropriate. Preferably an independent determination or verification is made at step 1200 as to whether or not each such biological sample is associated with the tested-for biological state, e.g. whether each sample was taken from a subject independently determined to have, or not to have, the disease, such as by a definitive diagnostic technique such as a biopsy or other clinical diagnostic. This independent determination and the sample characterization data for each of the additional samples may be input into a model update step 1300, along with the characterization data for the original set of known samples used to create the original model. A new or updated model can then be developed using the KDE techniques using this larger set of biologic samples of known state. The updated model may then be redeployed to be used in subsequent model determinations 1140.

Figure 2:
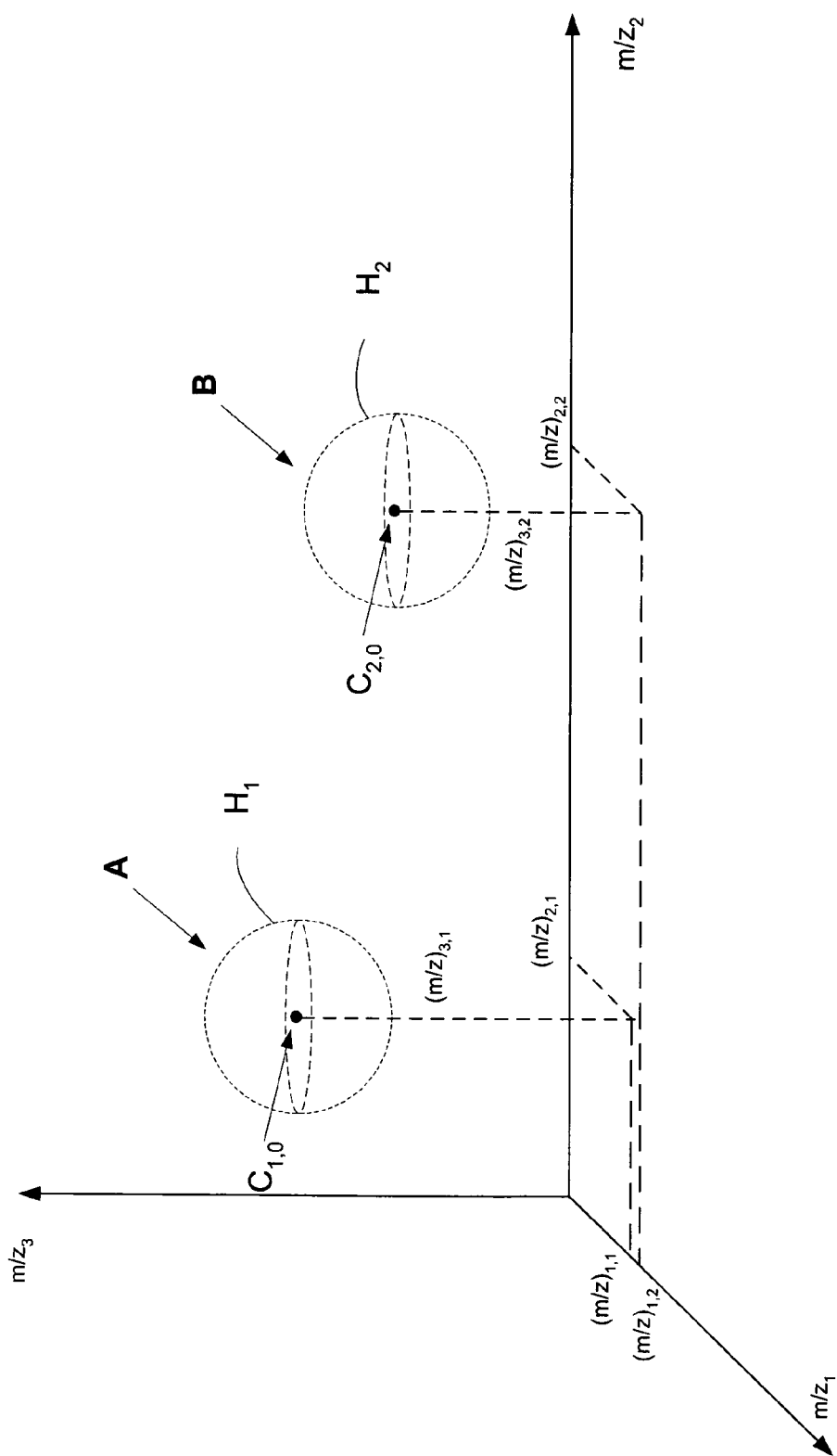
FIG. 2 is an example of a three-dimensional model including two clusters according to an embodiment of the invention.

FIG. 2 illustrates an exemplary model according to an aspect of the invention. While the model illustrated has two diagnostic clusters "A" and "B," plotted in three-dimensional space, the model can include any number of diagnostic clusters (preferably two or more diagnostic clusters) and any number of dimensions. Each of the diagnostic clusters is defined by a number (in this case, three) of vectors, each one of the vectors having a particular mass-to-charge value (which defines the corresponding dimension of the space) and an associated magnitude. While FIG. 2 illustrates the clusters "A" and "B" plotted in three-dimensional space, the number of dimensions is dictated by the number of vectors defining the cluster. Thus, the cluster is really a plot of multiple mass-to-charge values and magnitudes in n-dimensional space, where n corresponds to the number of features defining each cluster (i.e., the number of mass-to-charge values used in the model).

The cluster can be thought of as a sphere. In actuality, the cluster will probably be defined by a hypersphere or other hypervolume (for dimensions greater than three), but for ease of conceptualization, we will assume that the calculations explained herein are performed in three-dimensional space. Each cluster will be centered on a centroid, which is point defined in n-dimensional space by the sum of the vectors associated with the cluster.

FIG. 2 illustrates two centroids $C_{1,0}$ and $C_{2,0}$. Each centroid is designated by the letter C, followed by an ordered pair of numbers (i.e., $C_{i,j}$), where "i" is the cluster number, which can be arbitrarily designated and is used for description purposes only, and "j" is the iteration associated with monitoring the applicability of the model to the sample population. For example, j=0 designates that the location of the centroid of the original model, without taking into account the effect of any additional samples; j=1 connotes the location of the centroid taking into account the effect of data associated with one additional biological sample that maps to this centroid. This centroid is known as a "drift centroid." As the variable "j" increases, the number of additional biological samples (or adaptive modeling iterations) has increased (i.e., the amount of data associated with the location of each centroid and cluster has increased by additional samples). A hypervolume (in this case a sphere) $H_1$, $H_2$ having a predetermined radius may be defined centered on the centroid. This hypervolume defines a region within which, if a set of vectors abstracted from a data stream (e.g. a mass spectrum) associated with a new biological sample maps, the biological sample is assigned by the model the biological state associated with the cluster (e.g. "diseased" or "not diseased"). Each hypervolume $H_1$, $H_2$, represents one cluster in the diagnostic model.

An assessment can be made of whether the population from which the unknown samples are drawn for diagnosis by the model differs significantly from the population from which the samples on which the model was based were taken. When data associated with one or more new, unknown biological samples are received, in addition to (or instead of) comparing the data to the model for diagnostic purposes, the data can be input into the model monitoring software and compared to the model. In one embodiment, only one set of data is input into the software. The one set of data is associated with a single biological sample. The data are then plotted in n-dimensional space (or, as depicted, in three-dimensional space). For example, the vectors abstracted from the mass spectrum associated with the biological sample can map to a point other than points $C_{1,0}$ or $C_{2,0}$. The software can compare the model to the point actually plotted, and can determine the effect that the new data could have on the model.

In one embodiment, data associated with a given biological sample are run through the model once, although running the data through multiple times would be possible.

Figure 3:
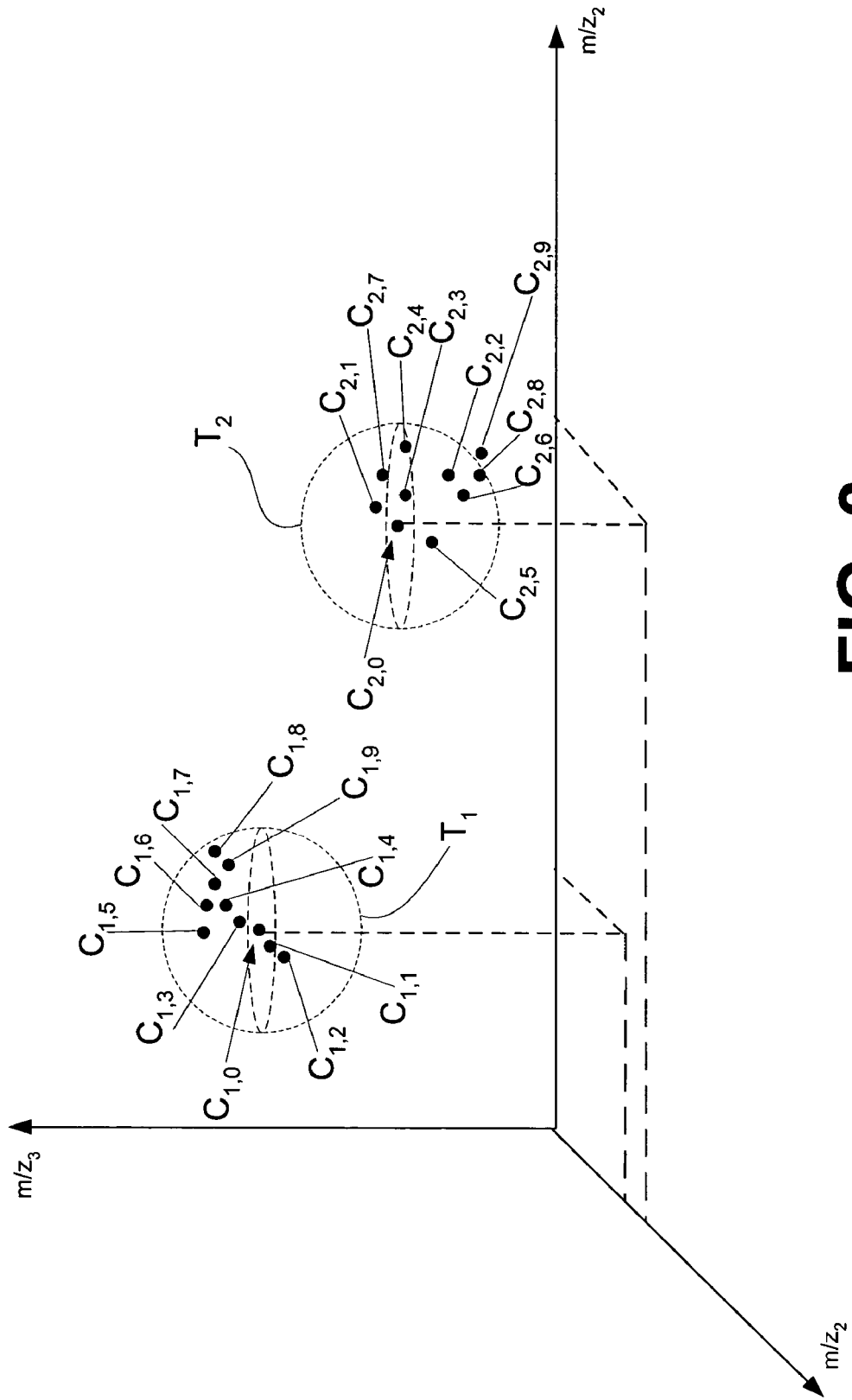
FIG. 3 is an example of a three-dimensional model and a recalculated position of a centroid when a number of samples are taken into account.

A three-dimensional plot of a monitored model drift is illustrated in FIG. 3. While the model illustrated in FIG. 3 is a three-dimensional model, the model in actuality can have n-dimensions. However, a three-dimensional model is illustrated for purposes of conceptualization.

In one example, a first set of data associated with a first biological sample can be used to modify the model's centroid locations. The location of the centroid of the first cluster may shift from a point $C_{1,0}$ to a point $C_{1,1}$ (or, if the sample instead maps into the second cluster, the centroid for the second cluster may shift from point $C_{2,0}$ to point $C_{2,1}$). This point is then compared with a predetermined tolerance, which can be, for example, a volume or a hypervolume defined by $T_1$ for the first centroid (or $T_2$ for the second centroid) (each of $T_1$ and $T_2$ being smaller than the radius of the respective hypervolume $H_1$, $H_2$).

The additional data from each sample input into the model after model developed will have a pro rata effect on the position of the centroid of a cluster. For example, a model can be constructed using 215 biological samples, of which 100 are associated with the first cluster and 115 are associated with the second cluster. After the model has been developed, each additional sample run through the model may be allowed to affect the position of the corresponding centroid. The drift centroid is defined as a mean of the vectors associated with all of the samples that correspond to the centroid's cluster, i.e. original 100 samples associated with the first cluster and the additional sample(s). Therefore, the first new biological sample will have a greater effect on the location of the first cluster's centroid than could then two-thousandth.

When a second set of data associated with a second biological sample are taken into account, the location of the first centroid may shift from point $C_{1,1}$ to a point $C_{1,2}$ (or the centroid for the second cluster may shift from point $C_{2,0}$ to a point $C_{2,1}$ if the second sample maps to the second cluster). As before, the updated location of the relevant centroid is then compared with the predetermined tolerances for the relevant cluster ($T_1$ or $T_2$).

When a third set of data associated with a third biological sample is taken into account, the location of, for example, the first centroid may shift from point $C_{1,2}$ to point $C_{1,3}$ (or the centroid for the second cluster may shift from point $C_{2,1}$ to a point $C_{2,1}$, if the third sample (and the second sample) maps to the second cluster. As before, the updated location of the relevant centroid is then compared with the predetermined tolerances for the relevant cluster ($T_1$ or $T_2$).

This method described above permits the user to monitor the consistency of the new samples with the samples on which the model was based, and thus to determine whether and when it may be appropriate to develop a new model. In the example illustrated in FIG. 3, the effect of eighteen different sets of data on the model's centroids (nine sets of data corresponding to each of the two clusters) is shown. These different sets of data cause the centroid associated with each of the two illustrated clusters to move to a new point, as described above. For example, the centroid associated with the first cluster may be located at $C_{1,4}$, and move to drift centroids $C_{1,5}$, $C_{1,6}$, $C_{1,7}$, $C_{1,8}$, and $C_{1,9}$ based on additional data associated with a fourth, fifth, sixth, seventh, eighth, and ninth data set that maps to that cluster, each data set being associated with a unique biological sample. Additionally, for example, the centroid associated with the second cluster may move to drift centroid $C_{2,9}$ based on the additional data associated with nine additional data sets that map to the second cluster, each data set being associated with a unique biological sample.

As illustrated in FIG. 3, the ninth sample caused the centroid to drift outside of the predetermined tolerance $T_2$ for the second cluster. Once a determination is made that the centroid has drifted outside of the predetermined tolerance, the model may be updated. Exemplary procedures for updating the model are discussed in more detail below. It is not necessary for both clusters to have a centroid that has drifted outside the predetermined tolerance, as is depicted in FIG. 3. For example, FIG. 3 illustrates an exemplary embodiment where only one cluster has a centroid that has moved outside of the predetermined tolerance (i.e., point $C_{2,9}$); point $C_{1,9}$, which is also associated with the ninth data sample for that cluster, did not fall outside of the predetermined tolerance $T_1$.

One example of a mathematical method of monitoring the drift of a centroid of a model involves comparing the distance between the drift centroid and the original centroid to determine if the distance exceeds a predetermined threshold. In the embodiment illustrated in FIG. 3, the distance between, for example, point $C_{1,0}$ and $C_{1,1}$ can be mathematically represented as:

$$d = |C_{1,0}(x, y, z)C_{1,1}(a, b, c)|$$
$$= \sqrt{(x-a)^2 + (y-b)^2 + (z-c)^2},$$

which is the mathematical representation of the distance between two centroids in three-dimensional space. This mathematical model may be further expanded to n-dimensional space, where n is the based on the number of vectors from the data set, as follows:

$$d = |C_{1,0}(m_1, m_2, \ldots, m_n)C_{1,1}(t_1, t_2, \ldots, t_n)|$$
$$= \sqrt{\sum_{i=1}^{n}(m_i - t_i)^2}.$$

This equation for the distance between two points can then be compared to a threshold to determine if the threshold condition is met. For example, if $$|C_{1,0}(m_1, m_2, \ldots m_n)C_{1,1}(t_1, t_2, \ldots, t_n)| \geq T_1,$$

drift centroid $C_{1,1}$ falls outside of the predetermined tolerance and the model needs to be updated. In the example illustrated in FIG. 3, this condition would not be satisfied for any of the centroids associated with the first cluster. However, the following inequality would be satisfied, signaling to the user that the model was in need of updating and refinement:

$$|C_{2,0}(m_1, m_2, \ldots m_n)C_{2,9}(t_1, t_2, \ldots, t_n)| \geq T_2.$$

While the mathematical method of monitoring the drift of the centroids due to the additional data sets has been described in terms of Cartesian mathematics, the drift may be monitored by a number of different mathematical constructs, including Euclidian distance calculations, Hamming distance calculations, and Mahalanbois distance calculations.

While the effect of nine additional sets of data for each cluster's centroid was illustrated in the foregoing example, it is to be understood that any number of data sets may be taken into account.

Figure 4:
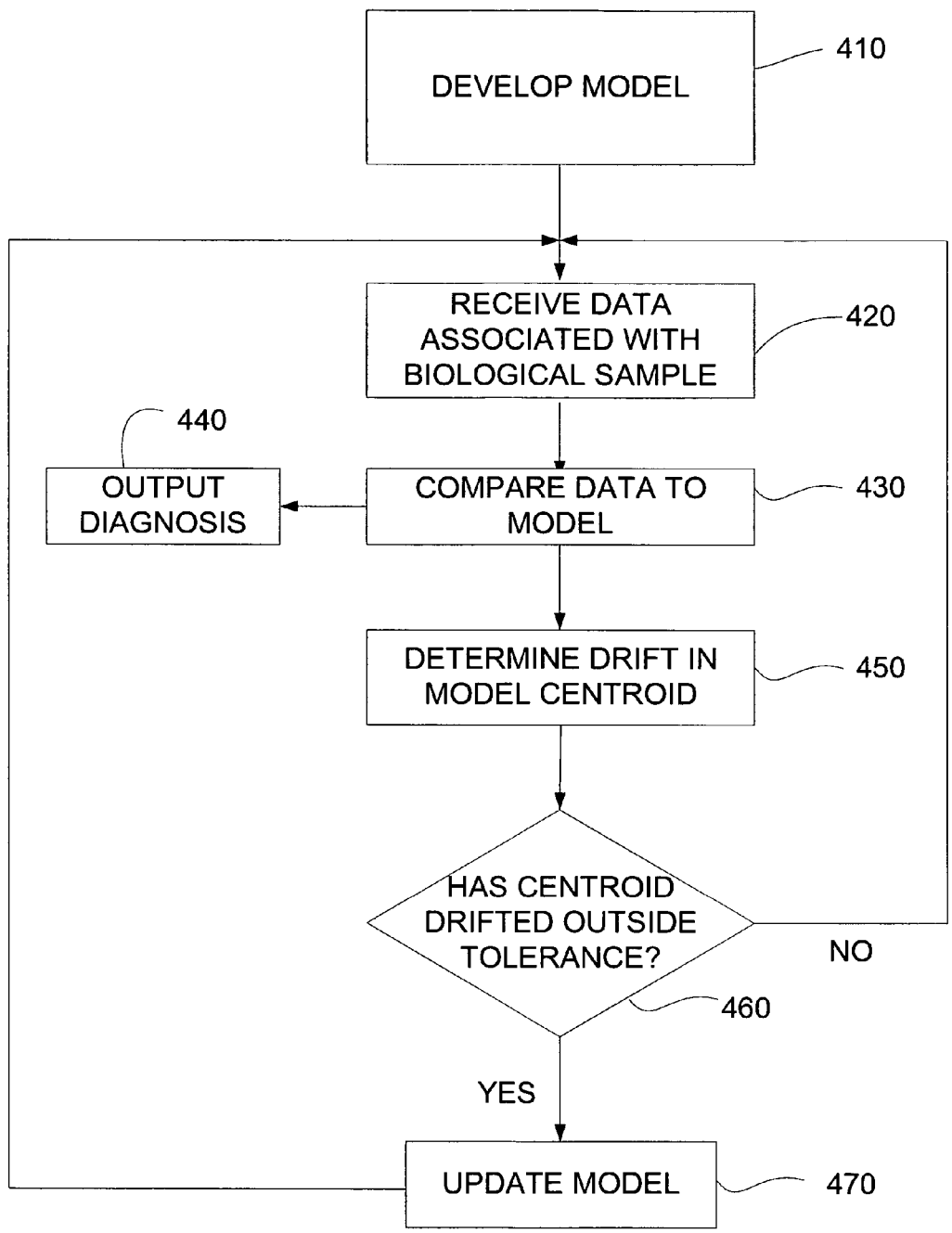
FIG. 4 is a flow chart illustrating a method including monitoring and updating a model according to one embodiment of the invention.
Figure 5:
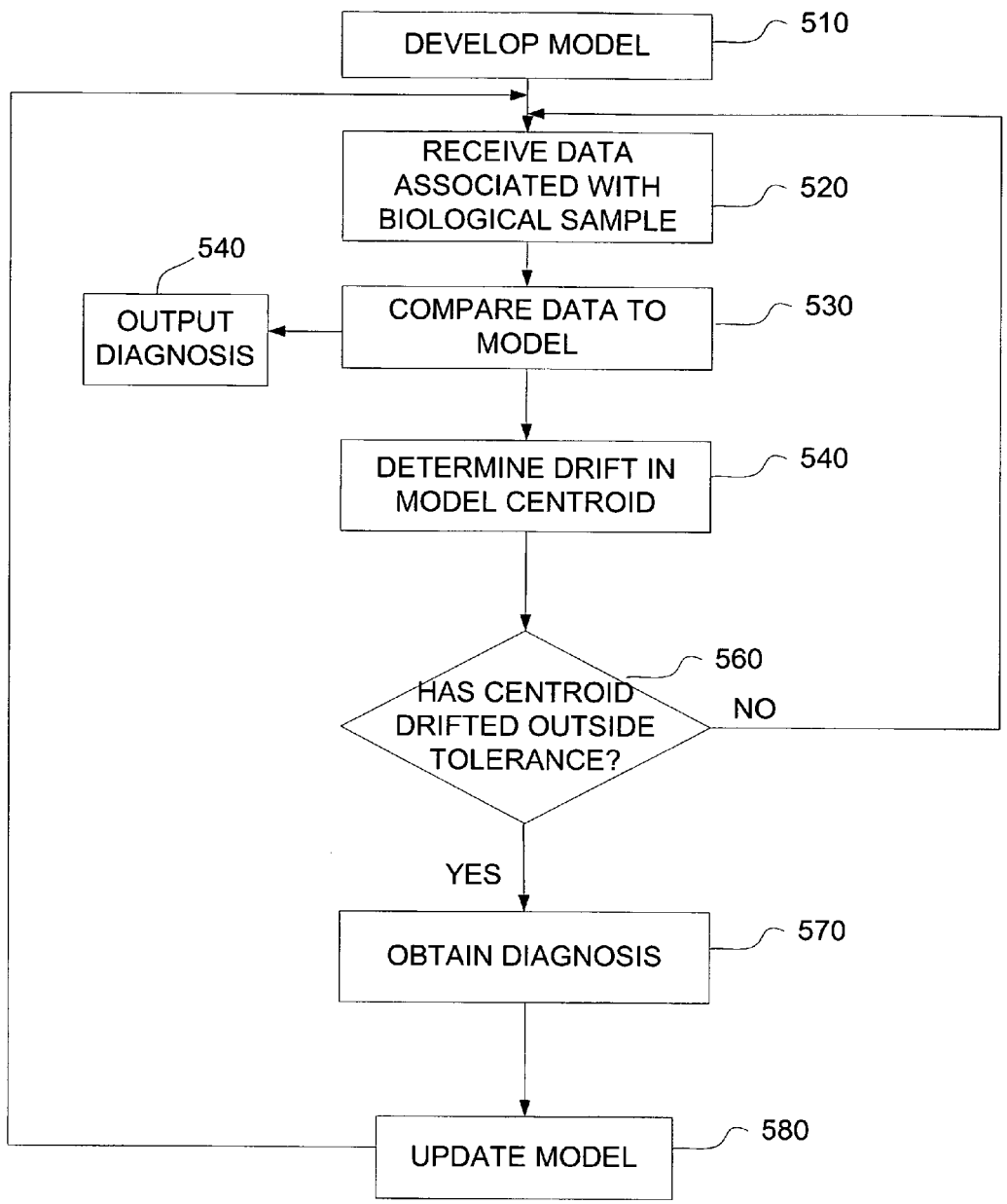
FIG. 5 is a flow chart illustrating a method including monitoring and updating a model according to another embodiment of the invention.

FIGS. 4 and 5 are flow charts of two exemplary methods of developing a model, monitoring a drift in the model's centroids, and refining the model. In the embodiment illustrated in FIG. 4, the model is developed, at step 410. As described above, the model can be developed as described in the Heuristic Methods patent application. Next, data associated with a biological sample may be received from a sample acquisition location, at step 420. In one embodiment, the data can be received over an Internet connection, for example, a wide area network (WAN), a local area network (LAN), or any other internet or intranet data communication means, including wireless communication of the data. These data can include a number of mass-to-charge values making up a mass spectrum and associated magnitudes that make up a mass spectrum associated with a particular biological sample. This mass spectrum may be based on any suitable protein separation technique, including, but not limited to MALDI, SELDI, electrospray ionization (ESI), or any other high-throughput processes. As described with respect to FIG. 6, below, the mass spectra data may be obtained at the sample acquisition location or the diagnostic location.

After the data associated with the biological sample has been received at the diagnostic location, at step 420, the data can be input into the model to determine whether the biological sample is associated with a particular disease state, at step 430. The diagnostic program can compare data received to the model developed in step 410 to determine a diagnostic and will then output that diagnosis, at step 440, as described in greater detail in the Hidden Patterns patent application.

In addition to determining if the biological sample is associated with a disease state, the continuing validity of the model can be monitored by determining the effect of the additional data on the centroid of the cluster to which the sample maps, as described above. The software can determine the drift of the model's relevant centroid at step 450. The software can then determine whether the amount of centroid drift exceeds the predetermined threshold, as described with reference to FIG. 3, at step 460. If the centroid has not drifted more than the predetermined threshold, the model is presumed to remains valid for use with the population from which the new samples are drawn, and additional data associated with additional biological samples may be received, at step 420. If the centroid has drifted by more than the predetermined tolerance, then the model is updated, at step 470, preferably by using the original data on which the model was based and on at least a subset of the new data received in step 420, preferably a subset for which definitive diagnoses of the relevant biological state (e.g. having or not having ovarian cancer) has been obtained. [Optionally, the model update could be performed using all samples that mapped into one of the original model's clusters and assuming that the model's diagnosis was correct.] The updated (or new) model can then be used to diagnose additional unknown samples.

The method illustrated in FIG. 5 differs from that of FIG. 4 in that a step of requesting a diagnosis is used before updating the model, step 570. As described with reference to FIG. 4, the original model is developed at step 510, and data associated with a particular biological sample is received at step 520. This received data is then input into the diagnostic software and compared to the model at step 530. The diagnostic software can then output a diagnosis at 540. As described with reference to FIG. 4, the drift in the relevant one of the model's centroids due to the acquisition of the new data associated with a biological sample can be calculated at step 520. Once the diagnostic software has determined that the centroid of a cluster in the model has drifted outside of a predetermined tolerance, and therefore that the model should be updated or recreated, a request may be made to, for example, a sample collection location or a physician, to obtain a definitive or clinical diagnosis of the patient from which each new biological sample was acquired, at step 570. The requested diagnosis can be independent of the diagnosis performed using the diagnostic software. Once the diagnosis has been received, the model may be updated or recreated (at step 580) using the data received in each iteration of step 520. Once the model has been updated, it may be redeployed, and may be used to diagnose additional biological samples for a disease state.

In one embodiment, the diagnosis is from a means that is independent of the diagnostic software, such as, for example, a biopsy for a cancerous disease state. Patients may be notified at the sample collection location that their sample will be utilized to monitor the model, and the patients may be asked to consent to this. Additionally, patients may be requested to sign a consent agreement permitting their independent diagnosis results (e.g., the results from their biopsy) to be used in updating the model. In one embodiment, only consenting patients will have their samples used to update the model.

Figure 6:
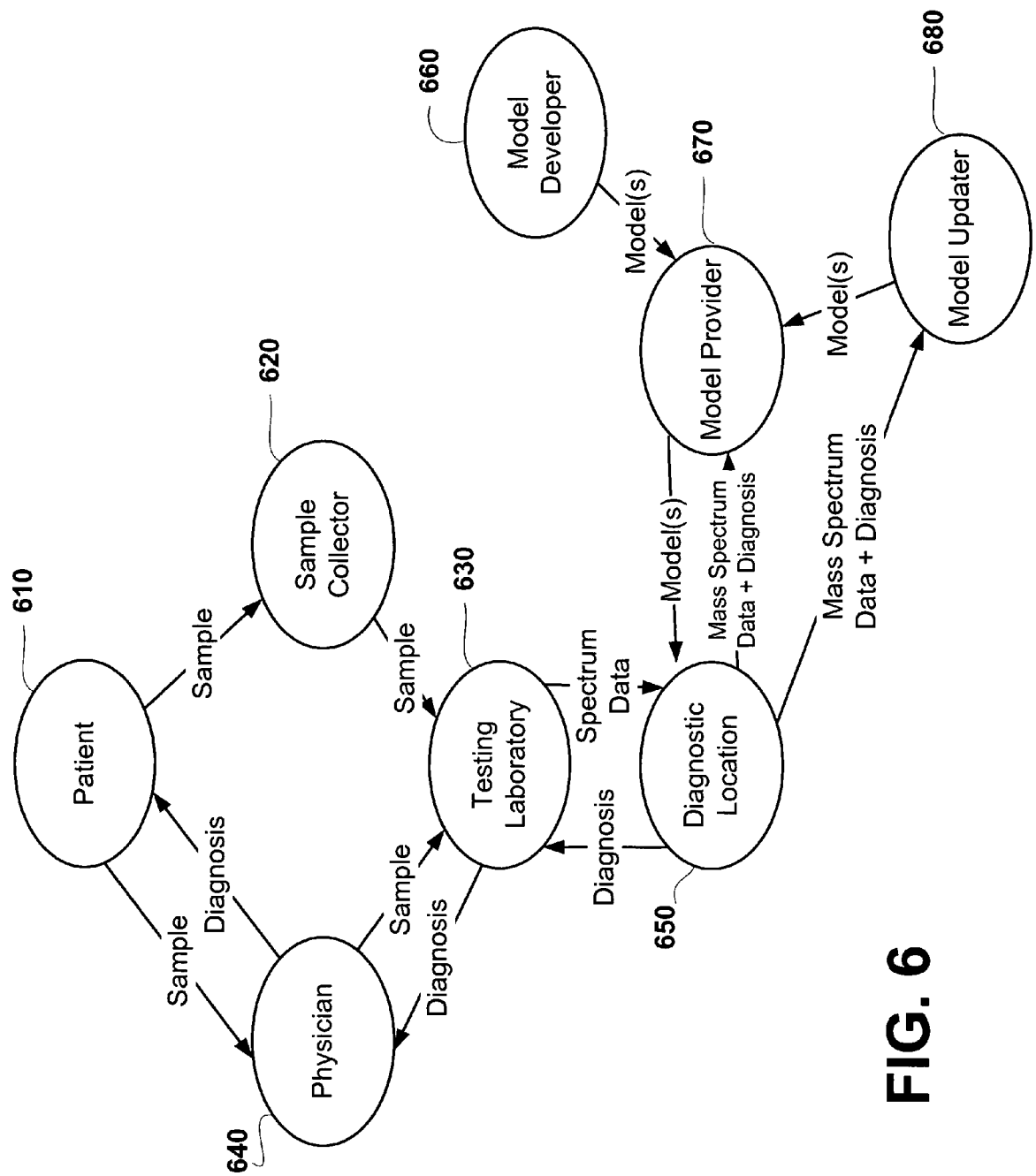
FIGS. 6 and 7 are diagrams illustrating various entities that may be involved in methods according to various embodiments of the invention, and possible relationships or interactions among the entities.

In applying the methods described above, various steps or portions of the method may be performed by different entities and/or at geographically dispersed locations, and various relationships may be defined among the different entities and/or locations. A diagram illustrating various entities and possible relationships among the entities is illustrated in FIG. 6. A patient 610 may go to a sample collector 620 at a sample collection location to have, for example, blood drawn. This blood is the biological sample described above. This blood may be sent to a testing laboratory 630 from the sample collection location 620.

Alternatively, as illustrated in FIG. 6, the patient 610 may go to a physician 640 to have the biological sample taken. The biological sample can be sent from the physician 640 to the testing laboratory 630. In one embodiment, the testing laboratory can obtain mass spectral data (or other bioassay data) associated with the biological sample. These results may be stored on a computer readable medium at the testing laboratory 630. Alternatively, the mass spectrum may be sent to the diagnostic location 650 using any electronic means of transport, including an internet or intranet connection, or a wireless network, or a diskette. The diagnostic software can then automatically receive the data, compare it to the model, and output a diagnosis to the testing laboratory 630 almost instantaneously (depending on the computing capabilities of the processors at the diagnostic location 650, and the bandwidth of the connection between the sample collection location 620 and the diagnostic location 650).

As described with reference to FIGS. 3-5, the model's validity for the population of subjects from which the samples are drawn can be monitored. In one embodiment, the model can be developed by a first entity, referred to herein as the model developer 660. The model developer may then permit the model to be distributed by a model provider 670. The model provider 670 can receive the mass spectrum data and the diagnosis from the diagnostic location 650 and can calculate drift centroids for the model based on the additional data received from the testing laboratory 630. If and when the drift in any centroid of the model exceeds a threshold amount, the model updater 680 can produce a refined model and provide that model to the model provider 670.

In the embodiment depicted in FIG. 6, the diagnostic location 650, the model provider 670, the model developer 660, and the model updater 680 are illustrated as separate entities. This does not need to be the case. For example, in another embodiment (not illustrated), the model provider 670, the model developer 660, and the model updater 680 can be the same entity. Additionally, this entity can also include diagnostic location 650. Therefore, there is no need to have separate entities for performing each of the functions illustrated in FIG. 6.

Additionally, while sample collector 620 and testing laboratory 630 are illustrated as separate entities, this is done so for illustration purposes only, and one of ordinary skill in the art will appreciate that sample collector 620 and testing laboratory 630 can be the same entity and be co-located.

Figure 7:
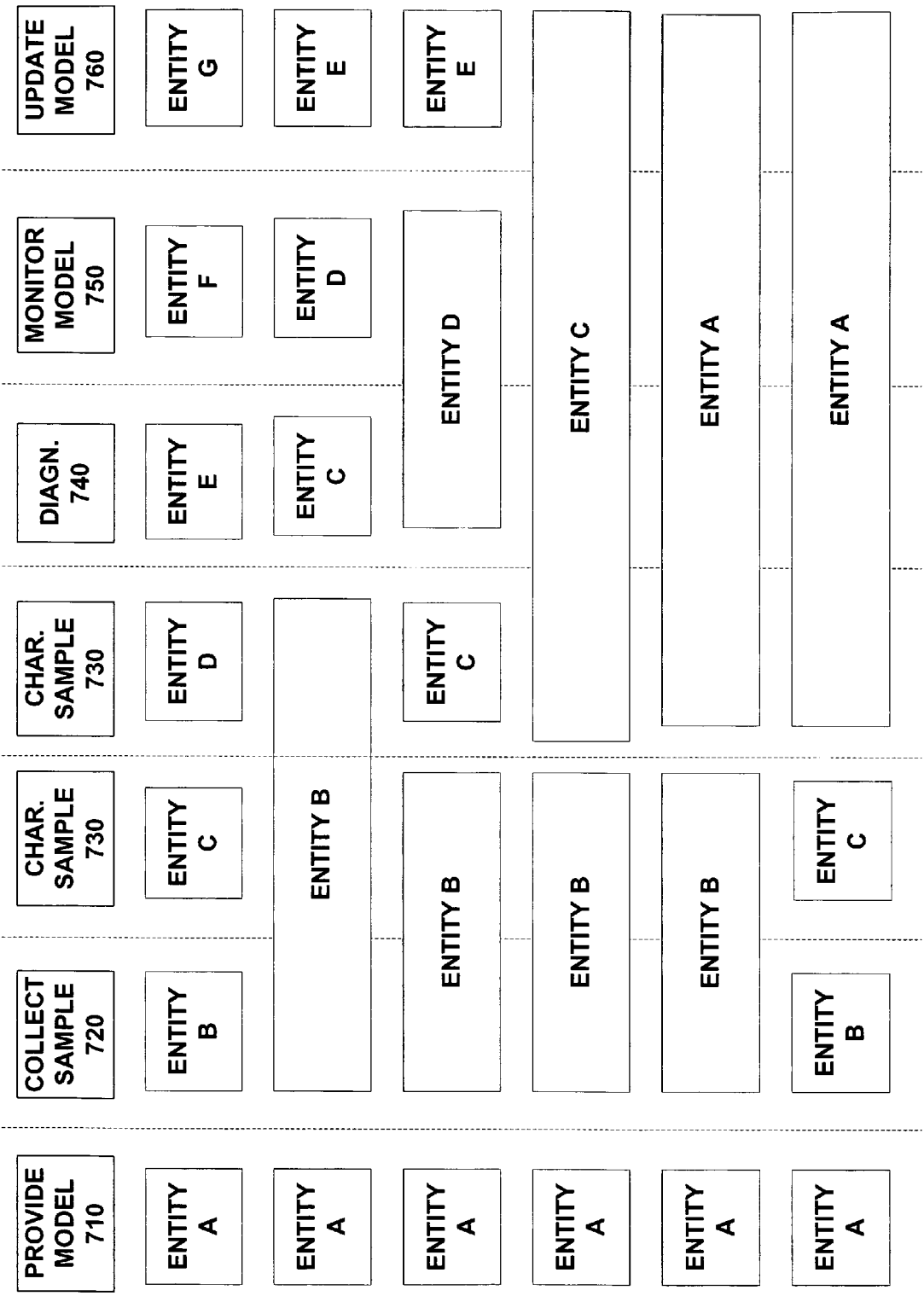

Some examples of possible distributions of the steps/functions described above among different entities are illustrated in FIG. 7. FIG. 7 depicts the various entities and a subset of possible permutations of relationships among different entities. In example 1, seven different entities can perform the different steps of providing the model 710, collecting the samples 720, characterizing the samples 730, abstracting the samples 740, diagnosing the samples 750, monitoring the model 760, and updating the model 770.

In example 2, the steps of sample collection 720, sample characterization 730, and sample abstraction 740 may be performed by the same entity, Entity B, while the other steps (providing the model 710, diagnosing the sample 750, monitoring the model 760 and updating the model 770), are each performed by separate entities.

In example 3, as in example 2, both the steps of sample collection 720 and sample characterization 730 can be performed by the same entity, Entity B. Additionally, the steps of sample abstraction 740, diagnosis 750 and monitoring the model 760 may be performed by the same entity, Entity C. Finally, in this example, the steps of providing the model 710 and updating the model 770 can be performed by two separate entities (Entity A and Entity D).

In example 4, as in examples 2 and 3, both the steps of sample collection 720 and sample characterization 730 can be performed by the same entity, Entity B. Additionally, the steps of sample abstraction 740, diagnosis 750, monitoring the model 760, and updating the model 770 may be performed be the same entity, Entity C. Finally, in this example, the step of providing the model 710 is performed by Entity A.

In example 5, as in examples 2-4, both the steps of sample collection 720 and sample characterization 730 can be performed by the same entity, Entity B, while the steps of providing the model 710, sample abstraction 740, diagnosis 750, monitoring the model 760, and updating the model 770 can be performed by Entity A.

In example 6, the step of sample collection 720 may be performed by Entity B, whereas the steps of sample characterization 730 and sample abstraction 740 may be performed by Entity C. As in example 5, the steps of providing the model 710, diagnosis 750, monitoring the model 760, and updating the model 770 can be performed by Entity A.

While general relationships have been described with reference to FIG. 7, these relationship are only meant to be exemplary, and not intended to be exclusive of the various other permutations of the specific examples depicted in FIG. 7, and described herein. For example, a single entity may perform all of the steps 710-770.

Figure 8:
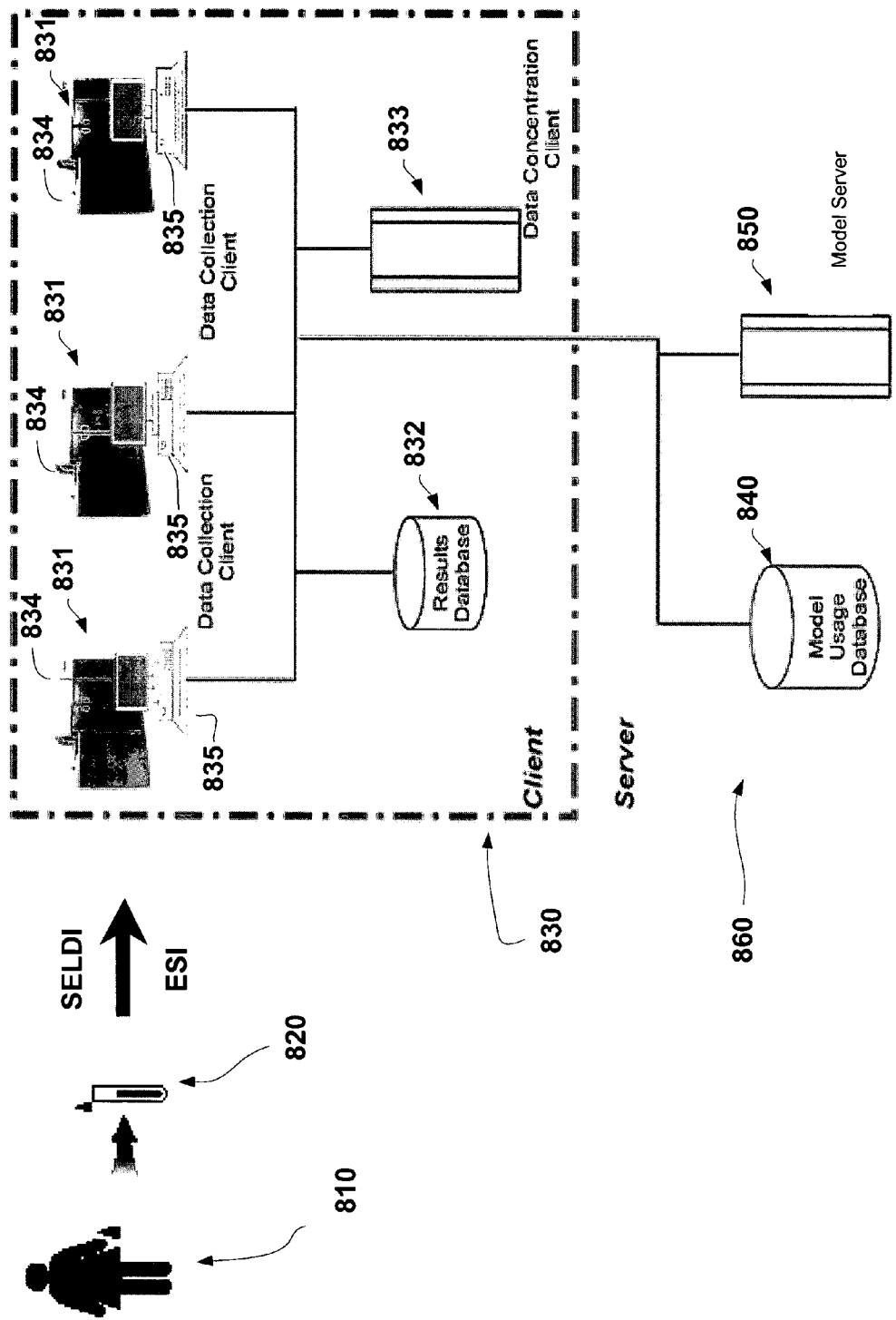
FIG. 8 illustrates a system for implementing the diagnostic methods using modeling software disclosed herein.

The general operation of an exemplary implementation of the methods set forth above will now be described. Sample characterization data (such as mass spectrum data) acquired from a particular biological sample can mapped against the model which can be configured to receive the information from multiple sample collection locations (as shown in FIG. 8) in real-time, and can analyze the data and provide substantially instantaneous diagnostic feedback to the laboratory, doctor's office, or other remote site. For example, in one embodiment, the diagnostic feedback is displayed at the remote site (such as on a display of a computer such as is described in more detail in connection with FIG. 10). In another embodiment, the diagnostic feedback may be sent to a result database. The result database may be accessed from the remote site to retrieve the diagnostic feedback. The sample characterization data may be sent over an internet, an intranet, or other electronic, high-speed connection to a server for processing and comparison with the model for a particular disease state.

Another embodiment in which the sample collection location can transmit relevant data to the diagnostic software in real-time over an internet or intranet connection permits the user at the sample collection location to select the diagnostic model(s) to which the sample is to be compared. For example, when a patient has a sample taken for analysis, the specific ailment or malady for which the sample should be tested may not yet be apparent to the physician. The sample characterization data associated with the biological sample may be compared to a number of different models in real-time or near real-time based on a selection made by the end-user at the sample collection location. For example, the end-user may desire to have the sample tested for three different types of cancer. Alternatively, the biological states tested for may include the presence of alcohol and/or a number of different narcotics in the blood. In yet another embodiment, the end-user may wish to test for the particular state of a disease, for example, the end-user may wish to determine if the particular disease tested for is in remission, has been cured, or is active. The abstraction of the relevant vectors from the characterization data may take place at the end-users location in response to the selection of the models to be used, thus permitting a potentially much smaller quantity of data to be transmitted to the entity/location making the comparison to the model.

For example, in one embodiment, the user's device (i.e., a computer with a mass spectrometer) collects data based on a biological sample of the user. The user can select the diagnostic model(s) to which the data that describes the biological sample is to be compared. Once the user selects the diagnostic model(s) to which the data describing the biological sample is to be compared, the user's device transmits the selection to the server (which may be located remotely from the user's device). The server then identifies and requests that the user's device transmits the information needed to compare the biological sample characterization data to the selected model(s). In one embodiment, the information needed to compare the biological sample characterization data to the selected model(s) is a subset of the data acquired at the user's location. The user's device then transmits the identified information to the server, the data is compared to the model at the server location, and the server transmits a diagnosis to the user's device. Thus, only a small amount of all the data collected by the end-user's device is transmitted to the server. In one embodiment, 10% of the data collected by the user's device is transmitted to the server. In another embodiment, more than 10% of the data collected by the user's device is transmitted to the server. In another embodiment, less than 10% of the data collected by the user's device is transmitted to the server. In yet another embodiment, less than 1% of the data collected by the user's device is transmitted to the server.

In another embodiment, all of the characterization data may be transmitted to, and the abstraction may be done by, the same entity/at the same location as the model comparison, based on a communication from the user of the model(s) to be used.

In an alternative embodiment, the sample characterization data can be acquired and sent via a removable computer-readable medium, for example an optical storage disk (such as a recordable compact disk (CD-R)) or a magnetic storage disk (such as a diskette)), or can be sent via mail to the diagnostic location. The information can then be compared to the model, and a diagnosis may be output and sent back to the laboratory, or sample collection location.

In yet another embodiment, the sample itself can be sent to the diagnostic location to have the sample characterization data obtained from the biological sample. The data can then be input into a computer and compared to the model. A diagnosis can then be output and given to the laboratory.

FIG. 8 illustrates a system for implementing the methods of diagnosing biological samples using a model, monitoring drift in the model's centroid(s) from newly acquired data associated with biological samples, and providing a diagnosis to a patient 810.

FIG. 8 illustrates an exemplary network backbone diagram according to an embodiment of the invention. The network may have one or more client portions 830 and a server portion 860. The, or each, client portion 830 may include a number of different data collection clients 831 that may be coupled to a data concentration client 833 and a results database 832. Server portion 860 may include a model usage database 840 and a model server 850.

In the embodiment illustrated in FIG. 8 a biological sample 820 may be withdrawn from a patient 810. The biological sample may then be sent to a data collection client 831. In one embodiment, data collection client 831 includes a mass spectrometer 834 and a computer workstation 835. Data collection client 831 will obtain sample characterization (mass spectral) data from, for example, biological sample 820, using the mass spectrometer 834. Mass spectrometer 834 may be any type of mass spectrometer and the protein separation processes used may include any of those identified above. Data collection client 831 also includes a workstation 835. Workstation 835 can be configured to extract features relevant to the deployed model(s), thereby abstracting the sample data. Workstation 835 may also include software code to perform a quality assurance or quality control process. The data associated with each sample can be coded with an appropriate sample identifier. The sample identifier can include for example an alpha-numeric code which can identify, for example, the sample collection location, the particular patient, and the model(s) to which the data are to be mapped.

While FIG. 8 depicts three data collection clients 831, there can be any number of data collection clients 831. In one embodiment, there can be a data collection client 831 in every city throughout the world. In another embodiment, workstation 835 may store data associated with a number of samples, and may transmit these data to the data concentration client 833 periodically. After the data have been determined to meet predetermined standards (i.e., are determined by a quality assurance program to be fit for comparison to a model), the data may be sent from the data collection client 831 to data concentration client 833. Data concentration client 833 can be configured to arrange the data received from data collection client 831 into packages. These packages are arrangements of data that may be readily identified and used by the model server. In one embodiment, data concentration client 833 can log the data received from data collection clients 831. Data concentration client 833 permits communication over a backbone network or other bus to the server portion 860 and may be the only means for the server portion to communicate with the data collection clients 831, which are located behind a firewall (connoted by the dashed line surrounding the client 830). Alternatively, data concentration client 833 may periodically access the model server (using, for example, an ISDN connection) and submit a number of different packages associated with different samples. In one embodiment, data concentration client 833 may submit packages to model server 850, for example, every hour.

Data concentration client 833 can be configured to transmit individual packages of data received from the data collection clients 831 to the model server 850. Model server 850 can identify the model identifier associated with the sample identifier and determine which model to map the sample against. The model server 850 can also be configured to perform the mapping of the data associated with the samples against the proper model after the model has been identified. Model server 850 can be configured to handle multiple models. In addition to mapping the data associated with the samples against the models, model server 850 can score the data. Data scoring is described in more detail in the Heuristic Methods patent application.

After the data have been mapped against the model, model server 850 can output the data to the model usage database 840. Model usage database 840 can store both the data and the scores associated with each package received by the model server 850. Model usage database 840 can output the package of data and the score of the data associated with the package to results database 832. The data output from model usage database 840 can be output with the same unique identifier that was associated with the data at the data collection client. Model usage database 840 may access results database 832 via a password. In one embodiment, the password may be stored in software code for performing the process.

End users at the data collection client 831 can query the results database 832, using for example, the unique sample identifier to receive the scored results. In one embodiment, the data collection client 831 may be configured to store, for example, a look-up table including list of patients that have not received results yet by the unique sample identification associated with the sample and data sent to data collection client 833. Workstation 835 may access this lookup table and may query the results database 832 with the unique sample identifier to determine if the scored test results have been uploaded to the results database 832. In one embodiment, this query may be performed periodically; for example, workstation may access the results database every ten minutes, every hour, every day, or any other acceptable time depending on the needs of the end-users.

In an alternative embodiment, data collection client 831, results database 832, the model usage database 840, and the model server 850 may be in the same machine. In this embodiment, there would be no need to have the components distributed across a communications network.

In another embodiment, each data collection client 831 may include its own results database 832. In this embodiment, each package of data can be sent from data collection client 831 directly to the model server 850 without the need for data concentration client 833. This embodiment will reduce the need for the samples to be physically transported to collection locations, and can establish a "turnkey system."

In yet another embodiment, a number of data collection clients 831 may be dispersed across a particular geographic location, for example, the country of Japan. In this embodiment, data collection clients 831 may be connected to a data concentration client 833 that packages the data associated with the sample before sending the packages to the model server. Additional data collection clients 831 may be spread across, for example, Europe and may send the data to a data concentration client 833 associated with the European data collection clients 833. In this embodiment, each geographic area, for example, a nation, a continent, etc. may have its own data concentration client 833. The data concentration client can package the data and send the data off to a central model server 850. In an alternative embodiment, a model server 850 may be located in each geographical location.

As described above, the methods of the invention employ a single diagnostic model to diagnose a biological state of an individual biological sample. An alternative approach, which may be used with any of the methods above in lieu of a single model, employs multiple models to diagnose a biological state of interest for an individual biological sample. This approach is illustrated schematically in FIG. 9. In this approach, sample characterization data (such as mass spectral data) associated with a biological sample may be input into a redundant model, or a "super" model 910, which incorporates two or more individual models. In the embodiment illustrated in FIG. 9, redundant model 910 includes individual models 911, 912, 913. The individual models 911, 912, 913 may have a different number of dimensions, may have dimensions based on different features for the biological samples, different numbers and/or locations of clusters in their respective spaces, and different specificity and sensitivity. It may be particularly advantageous to combine individual models having different specificity and sensitivity. For example, the first model 911 can have the lowest sensitivity and specificity, the third model 913 can have a higher sensitivity and specificity than the first model 911 and the second model 912, whereas the second model 912 can have a higher sensitivity and specificity than the first model 911, but not the third model 913. The order of the models and the relative sensitivities and specificities are only exemplary, and any number of arrangements of models having differing sensitivities and specificities may be employed.

When the abstracted characterizing data for a biological sample (the abstraction step yielding all of the vectors needed for the individual component models of the redundant model 910) are input into redundant model 910, the data will be run through each of the three models, and each model produce a diagnosis at output 920. For example, the first model 911 can have a first output 921, the second model 912 can have a second output 922, and the third model 913 can have a third output 923.

Figure 9:
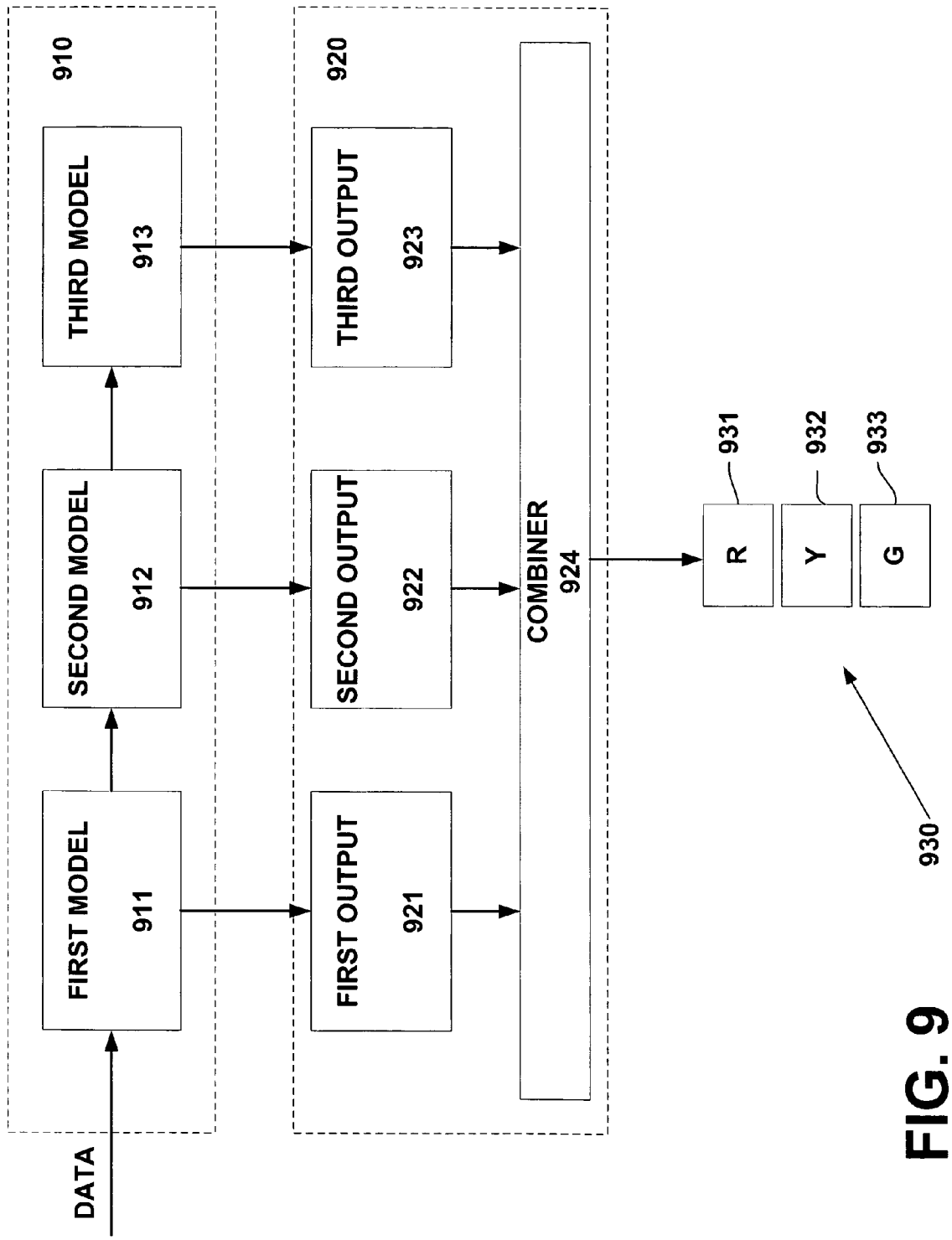
FIG. 9 illustrates a redundant "super" model according to an embodiment of the invention.

In the embodiment depicted in FIG. 9, the first, second, and third outputs can be combined via combiner 924 to give a single indication of the diagnosis and how accurate the particular diagnosis is (or how high the level of confidence in the diagnosis is). This may be done, for example, by a color-coded indicator. In this embodiment, a color-coded output display 930 is used. The color-coded display may display, for example, the colors red 931, yellow 932, and green 933. In one embodiment, when the output is red 931, each of the three models 911, 912, and 913 output a positive diagnosis for the tested for disease state. When the output is yellow 932, any one or two of the models (e.g., 911, 912) returned a positive diagnosis for the tested for disease state. When the output is green 933, none of the models 911, 912, and 913 output a positive diagnosis for the tested for disease state.

In an embodiment of the invention using a redundant model, the accuracy of the diagnosis may be improved. However, the accuracy of the overall model (in FIG. 9, the redundant model 910) may entail the sacrifice of computing speed because the processor must now compare the abstracted data to a number of different models. This may be compensated for, however, by using parallel processing technology, as well as by adapting the number of models 911, 912, and 913 used in the redundant model 910.

While the biological sample has been described above as being blood, any biological sample may be analyzed using any suitable bioassay process. For example, in addition to the use of blood as the biological sample, the biological sample may be any one of serum, saliva, plasma, nipple aspirants, synovial fluids, cerebrospinal fluids, sweat, urine, fecal matter, tears, bronchial lavage, swabbings, needle aspirants, semen, vaginal fluids, pre-ejaculate, tissue culture supertnatants, lypholized tissue cultures, and viral cultures. A biological sample may also be gaseous, rather than liquid, and may be extracted from a subject (such as a mammal), acquired from a space external to a subject, or simply taken from an area of interest, such as a public space or a cargo container (where the model is to analyze the area of interest rather than a subject).

While redundant modeling was described with reference to FIG. 9 as having three models 911, 912, and 913, any number of models may be used in the redundant model. For example, four, five, or any other number of models may be employed. Additionally, while the output to the end-user was described as a color-coded display, any type of output may be used. For example, a detailed chart illustrating the results for each model may be provide to and/or displayed at an end-user's computer. Alternatively, a detailed printout may be sent to the end-user. Other types of output other than visual output are also possible, for example, audible output to alert the end-user of the diagnosis may be used rather than, or in conjunction with, visual output.

Figure 10:
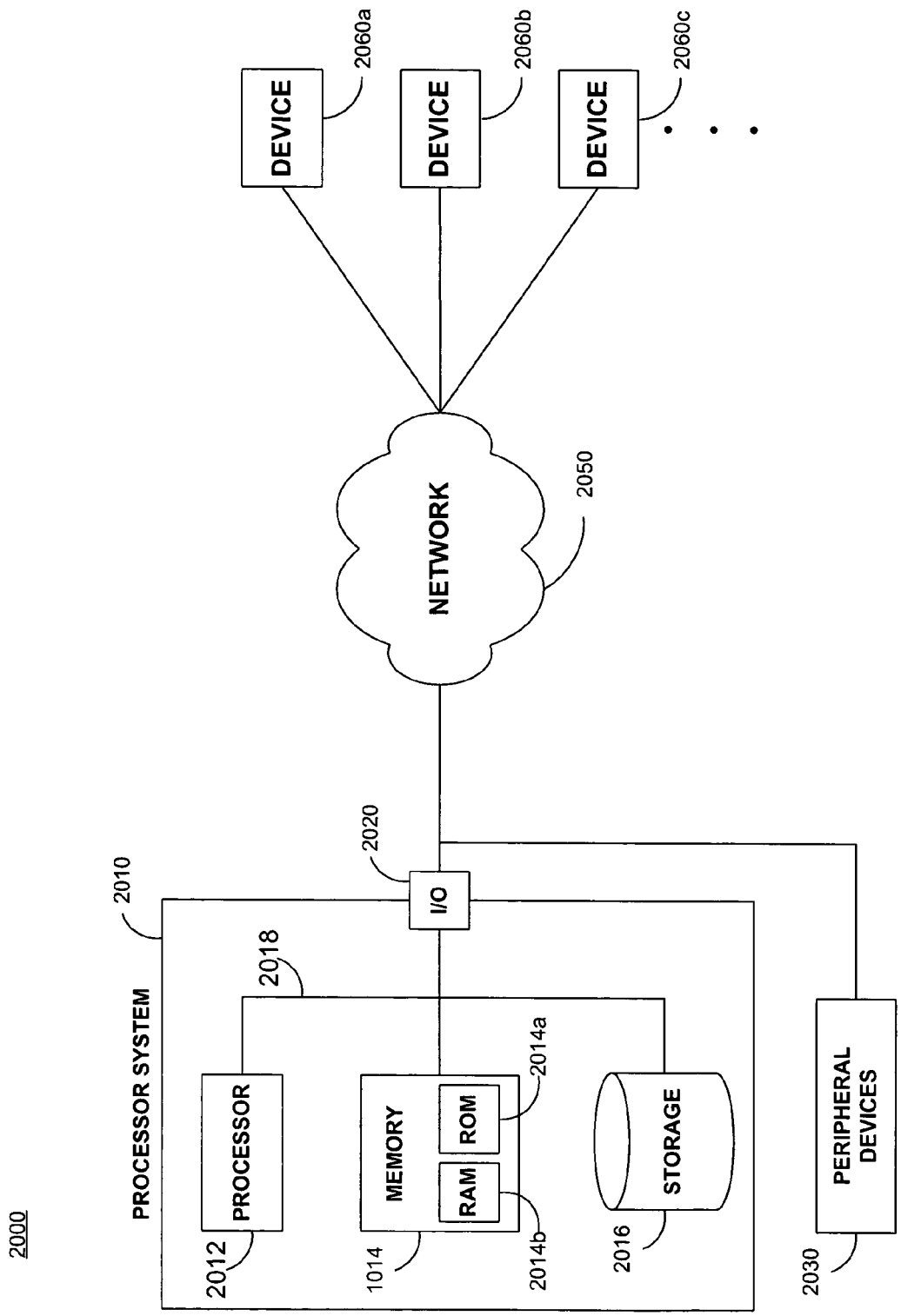
FIG. 10 is a schematic illustration of a computer system that may be used to perform methods or portions of methods according to embodiments of the invention.

FIG. 10 is a block diagram showing an example of a network system 2000 including processor system 2010 and other devices 2060a, 2060b, 2060c (referred to herein collectively, individually, or as a subset as device(s) 2060) connected to a network 2050, that may be used to execute the methods and/or software of the disclosed invention. The various elements in FIG. 10 are shown in a network-computing environment 2000, wherein a processor system 2010 is interconnected with a network 2050, by which the processor system 2010 and/or multiple other devices 2060 can communicate. It will be appreciated that the elements shown in FIG. 10 are examples of components that can be included in such a processor system 2010 and/or devices that can be in communication with a processor system 2010, and that elements can be removed or additional elements can be added depending upon the desired functionality of such a system. For example, the processor system 2010 can function independently of a network 2050, or can include more or fewer components than illustrated in FIG. 10.

The processor system 2010 illustrated in FIG. 10 can be, for example, a commercially available personal computer (PC), a workstation, a network appliance, a portable electronic device, or a less-complex computing or processing device (e.g., a device that is dedicated to performing one or more specific tasks or other processor-based), or any other device capable of communicating via a network 2050. Although each component of the processor system 2010 is shown as a single component in FIG. 10, the processor system 2010 can include multiple numbers of any component shown in FIG. 10. Additionally, multiple components of the processor system 2010 can be combined as a single component, where desired.

The processor system 2010 includes a processor 2012, which can be a commercially available microprocessor capable of performing general processing operations. For example, the processor 2012 can be selected from the 8086 family of central processing units (CPUs) available from Intel Corp. of Santa Clara, Calif., or other similar processors. Alternatively, the processor 2012 can be an application-specific integrated circuit (ASIC), or a combination of ASICs, designed to achieve one or more specific functions, or enable one or more specific devices or applications. In yet another alternative, the processor 2012 can be an analog or digital circuit, or a combination of multiple circuits.

The processor 2012 can optionally include one or more individual sub-processors or coprocessors. For example, the processor 2012 can include a graphics coprocessor that is capable of rendering graphics, a math coprocessor that is capable of efficiently performing mathematical calculations, a controller that is capable of controlling one or more devices, a sensor interface that is capable of receiving sensory input from one or more sensing devices, and so forth.

Additionally, the processor system 2010 can include a controller (not shown), which can optionally form part of the processor 2012, or be external thereto. Such a controller can, for example, be configured to control one or more devices associated with the processor system 2010. For example, a controller can be used to control one or more devices integral to the processor system 2010, such as input or output devices, sensors, or other devices. Additionally, or alternatively, a controller can be configured to control one or more devices external to the processor system 2010, which can be accessed via an input/output (I/O) component 2020 of the processor system 2010, such as peripheral devices 2030, devices accessed via a network 2050, or the like.

The processor system 2010 can also include a memory component 2014. As shown in FIG. 10, the memory component 2014 can include one or more types of memory. For example, the memory component 2014 can include a read-only memory (ROM) component 2014a and a random-access memory (RAM) component 2014b. The memory component 2014 can also include other types of memory not illustrated in FIG. 10 that are suitable for storing data in a form retrievable by the processor 2012, and are capable of storing data written by the processor 2012. For example, erasable programmable read only memory (EPROM), electrically erasable programmable read only memory (EEPROM), flash memory, as well as other suitable forms of memory can be included as part of the memory component 2014. The processor 2012 is in communication with the memory component 2014, and can store data in the memory component 2014 or retrieve data previously stored in the memory component 2014.

The processor system 2010 can also include a storage component 2016, which can be one or more of a variety of different types of storage devices. For example, the storage component 2016 can be a device similar to the memory component 2014 (e.g., EPROM, EEPROM, flash memory, etc.). Additionally, or alternatively, the storage component 2016 can be a magnetic storage device (such as a disk drive or a hard-disk drive), a compact-disc (CD) drive, a database component, or the like. In other words, the storage component 2016 can be any type of storage device suitable for storing data in a format accessible to the processor system 2010.

The various components of the processor system 2010 can communicate with one another via a bus 2018, which is capable of carrying instructions from the processor 2012 to other components, and which is capable of carrying data between the various components of the processor system 2010. Data retrieved from or written to the memory component 2014 and/or the storage component 2016 can also be communicated via the bus 2018.

The processor system 2010 and its components can communicate with devices external to the processor system 2010 by way of an input/output (I/O) component 2020 (accessed via the bus 2018). According one or more embodiments of the invention, the I/O component 2020 can communicate using a variety of suitable communication interfaces and protocols. The I/O component 2020 can also include, for example, wireless connections, such as infrared ports, optical ports, Bluetooth wireless ports, wireless LAN ports, or the like. Additionally, the I/O component 2020 can include, wired connections, such as standard serial ports, parallel ports, universal serial bus (USB) ports, S-video ports, large area network (LAN) ports, small computer system interface (SCSI) ports, and so forth.

By way of the I/O component 2020 the processor system 2010 can communicate with devices external to the processor system 2010, such as peripheral devices 2030 that are local to the processor system 2010, or with devices that are remote to the processor system 2010 (e.g., via the network 2050). The I/O component 2020 can be configured to communicate using one or more communications protocols used for communicating with devices, such as the peripheral devices 2030. The peripheral devices 2030 in communication with the processor system 2010 can include any of a number of peripheral devices 2030 desirable to be accessed by or used in conjunction with the processor system 2010. For example, the peripheral devices 2030 with which the processor system 2010 can communicate via the I/O component 2020, can include a communications component, a processor, a memory component, a printer, a scanner, a storage component (e.g., an external disk drive, disk array, etc.), or any other device desirable to be connected to the processor system 2010.

The processor system 2010 can communicate with a network 2050, such as the Internet or other networks, by way of a gateway (not shown), a point of presence (POP) (not shown), or other suitable means. Other devices 2060 can also access the network 2050, and can be similar to or different from the processor system 2010. Additionally, the other devices 2060 can communicate with the network 2050 (and devices connected thereto) using a network service provider (NSP), which can be an Internet service provider (ISP), an application service provider (ASP), an email server or host, a bulletin board system (BBS) provider or host, a point of presence (POP), a gateway, a proxy server, or other suitable connection point to the network 2050 for the devices 2060.

The various features of the invention have been described in relation to a method of diagnosis of disease states by comparing bioassay data (such as mass spectrum data). In some embodiments, the model is adaptive. In other embodiments, the model is redundant. In yet other embodiments, the model may be both redundant and adaptive. Furthermore, the invention may involve interactions among multiple separate entities, each performing particular steps or portions of the overall processes. However, it will be appreciated that many of the steps may be implemented with various apparatus and bioinformatics methods and may be performed by any number of different entities, including a single entity. Moreover, variations and modifications exist that would not depart from the scope and spirit of the invention.

What is claimed is:

1. A computer implemented method of determining whether a diagnostic model is accurately applicable to a population of subjects to which the model is applied, the model being configured to determine a biological state of a subject, the model being based on a set of data streams, each of the data streams being obtained by performing an analysis of biological samples taken from subjects of known biological states, the model having at least one diagnostic cluster located in a vector space having at least three dimensions, each dimension corresponding to a vector common to the data streams in the set of data streams, the diagnostic cluster having a centroid located at an initial centroid location based on locations of vectors from the set of data streams that correspond to the diagnostic cluster, comprising:

receiving a vector set, the vector set including at least three vectors from a data stream obtained by performing the analysis of a biological sample taken from a subject of an unknown biological state;

mapping the unknown vector set into the vector space using a suitably programmed computer;

if the unknown vector set maps into the diagnostic cluster, calculating an updated location of the cluster centroid based on a combination of the location of the vectors from the unknown vector set and the set of data streams that correspond to the diagnostic cluster;

determining the distance between the initial centroid location and the updated centroid location; and if the distance between the initial centroid location and the updated centroid location is greater than a predetermined threshold, providing an output indicating that the threshold has been exceeded which is indicative that the diagnostic model is not accurately applicable to the population of subjects to which the model is applied.

2. The method of claim 1, further comprising;

if the distance between the initial centroid location and the updated centroid location is greater than the predetermined threshold, creating a new diagnostic model based on a combination of the unknown vector set and the data streams that correspond to the biological samples of known biological states from the population of subjects to which the model is applied.

3. The method of claim 1, wherein the output is a visual output.

4. The method of claim 1, the output being a first output, further comprising:

if the distance between the initial centroid location and the updated centroid location is less than the threshold, providing a second output indicating that the threshold has not been exceeded which is indicative that the diagnostic model is accurately applicable to the population of subjects to which the model is applied.

5. A method of determining whether a diagnostic model is sufficiently representative of a first population of subjects to which the model is applied, the model being configured to determine a biological state of a subject from the first population of subjects, the model being based on a set of data streams, each of the data streams being obtained by performing an analysis of biological samples taken from a second population of subjects, the second population of subjects being different than the first population of subjects, the second population of subjects being of known biological states, the model having at least one diagnostic cluster located in a vector space, the diagnostic cluster having an initial centroid located at an initial centroid location based the set of data streams obtained by performing the analysis of the biological samples taken from the second population of subjects, comprising:

receiving a data stream obtained by performing the analysis of a biological sample taken from a first subject of the first population, the first subject of the first population being of an unknown biological state;

receiving a data stream obtained by performing the analysis of a biological sample taken from a second subject of the first population, the second subject of the first population being of an unknown biological state;

mapping the first data stream and the second data stream into the vector space using a suitably programmed computer;

if the first data stream and the second data stream map into the diagnostic cluster, calculating an updated location of the cluster centroid based on a combination of the first data stream, and second data stream, and the set of data streams obtained by performing the analysis of the biological samples taken from the second population of subjects;

determining the distance between the initial centroid location and the updated centroid location; and if the distance between the initial centroid location and the updated centroid location is greater than a predetermined threshold, providing an output indicating that the threshold has been exceeded which is indicative that the diagnostic model is not sufficiently representative of the first population of subjects.

6. The method of claim 5, wherein the output is a visual output.

7. The method of claim 5, further comprising a step in which the determining is performed in a self monitoring process.

* * * * *